United States Patent [19]

Richards et al.

[11] Patent Number: 5,607,414
[45] Date of Patent: Mar. 4, 1997

[54] CATAMENIAL ABSORBENT STRUCTURES HAVING THERMALLY BONDED LAYERS FOR IMPROVED HANDLING OF MENSTRUAL FLUIDS, AND THEIR USE IN CATAMENIAL PADS HAVING IMPROVED FIT AND COMFORT

[75] Inventors: Mark R. Richards, Middletown; John R. Noel, Cincinnati; Larry N. Mackey; Yann-Per Lee, both of Fairfield; Anna R. Haney, Cincinnati; John L. Hammons, Hamilton; Susan N. W. Lloyd, Cincinnati, all of Ohio; Sheri D. Keeler, West Harrison, Ind.

[73] Assignee: The Procter & Gamble Company, Cincinnati, Ohio

[21] Appl. No.: 479,096

[22] Filed: Jul. 3, 1995

Related U.S. Application Data

[63] Continuation of Ser. No. 141,156, Oct. 21, 1993, abandoned.

[51] Int. Cl.$^6$ .............................. A61F 13/15; A61F 13/20
[52] U.S. Cl. .......................... 604/378; 604/358; 604/365; 604/366; 604/368; 604/370; 604/372
[58] Field of Search ........................ 604/358, 365–370, 604/372, 378, 379, 385.1

[56] References Cited

U.S. PATENT DOCUMENTS

| | | |
|---|---|---|
| 3,442,268 | 5/1969 | Bird . |
| 3,763,863 | 10/1973 | Mesek et al. . |
| 3,768,480 | 10/1973 | Mesek et al. . |
| 3,779,246 | 12/1973 | Mesek et al. . |
| 3,938,522 | 2/1976 | Repke . |
| 3,965,904 | 6/1976 | Mesek et al. . |
| 4,102,340 | 7/1978 | Mesek et al. . |
| 4,103,062 | 7/1978 | Aberson et al. . |

(List continued on next page.)

FOREIGN PATENT DOCUMENTS

| | | |
|---|---|---|
| 1230703 | 12/1987 | Canada . |
| 158914 | 10/1985 | European Pat. Off. . |
| 337296 | 10/1989 | European Pat. Off. . |
| 359501 | 3/1990 | European Pat. Off. . |
| 410480 | 1/1991 | European Pat. Off. . |
| 481322 | 4/1992 | European Pat. Off. . |
| 518340 | 12/1992 | European Pat. Off. . |
| 518291 | 12/1992 | European Pat. Off. . |
| 540041 | 5/1993 | European Pat. Off. . |
| 4024053 | 1/1992 | Germany . |
| 5/68693 | 3/1993 | Japan . |
| 1427199 | 3/1976 | United Kingdom . |
| 1547524 | 6/1979 | United Kingdom . |
| 2168612 | 12/1984 | United Kingdom . |
| 2266465 | 11/1993 | United Kingdom ............ 604/365 |
| 2269109 | 2/1994 | United Kingdom ............ 604/365 |
| 91/11162 | 8/1991 | WIPO . |
| 92/14430 | 9/1992 | WIPO . |

*Primary Examiner*—John G. Weiss
*Assistant Examiner*—P. Zuttarelli
*Attorney, Agent, or Firm*—Eric W. Guttag; Carl J. Roof; E. Kelly Linman

[57] ABSTRACT

Thermally bonded absorbent structures for catamenial products, in particular catamenial pads, that provide improved ability in acquiring, distributing and storing aqueous body fluids, especially menstrual fluids, as well as better fit and comfort for the user of the products. These structures comprise an optional thermally bonded secondary topsheet, a thermally bonded absorbent core having a relatively higher capillary suction primary fluid distribution layer, an optional but preferred relatively lower capillary suction secondary distribution layer, a storage layer having absorbent gelling material, and an optional fibrous "dusting" layer. These thermally bonded absorbent structures are particularly useful with catamenial pads having a primary fluid pervious topsheet selected from apertured formed film topsheets and high loft nonwoven topsheets.

67 Claims, 6 Drawing Sheets

U.S. PATENT DOCUMENTS

| | | |
|---|---|---|
| 4,186,165 | 1/1980 | Aberson et al. . |
| 4,259,958 | 4/1981 | Goodbar . |
| 4,260,443 | 4/1981 | Lindsay et al. . |
| 4,282,874 | 8/1981 | Mesek . |
| 4,315,721 | 2/1982 | Sorenson . |
| 4,331,730 | 5/1982 | Sorenson . |
| 4,338,371 | 7/1982 | Dawn et al. ............................ 604/368 |
| 4,360,021 | 11/1982 | Stima . |
| 4,370,289 | 1/1983 | Sorenson . |
| 4,414,255 | 11/1983 | Tokuyama et al. . |
| 4,425,126 | 1/1984 | Butterworth et al. . |
| 4,461,621 | 7/1984 | Karami et al. . |
| 4,467,012 | 8/1984 | Pedersen et al. . |
| 4,496,358 | 1/1985 | Karami et al. . |
| 4,500,315 | 2/1985 | Pieniak et al. . |
| 4,537,590 | 8/1985 | Pieniak et al. . |
| 4,540,454 | 9/1985 | Pieniak et al. . |
| 4,541,945 | 9/1985 | Allison . |
| 4,544,596 | 10/1985 | Holtman . |
| 4,548,856 | 10/1985 | Ali Khan et al. . |
| 4,551,191 | 11/1985 | Kock et al. . |
| 4,573,988 | 3/1986 | Pieniak et al. . |
| 4,578,068 | 3/1986 | Kramer et al. . |
| 4,578,070 | 3/1986 | Holtman . |
| 4,590,114 | 5/1986 | Holtman . |
| 4,596,567 | 6/1986 | Iskra . |
| 4,600,458 | 7/1986 | Kramer et al. . |
| 4,605,402 | 8/1986 | Iskra . |
| 4,624,819 | 11/1986 | Hartog et al. . |
| 4,634,621 | 1/1987 | Manning et al. . |
| 4,636,209 | 1/1987 | Lassen . |
| 4,640,810 | 1/1987 | Laursen et al. . |
| 4,652,484 | 3/1987 | Shiba et al. . |
| 4,699,620 | 10/1987 | Bernardin . |
| 4,715,918 | 12/1987 | Lang . |
| 4,761,322 | 8/1988 | Raley . |
| 4,765,812 | 8/1988 | Homonoff . |
| 4,838,885 | 6/1989 | Bernardin . |
| 4,851,069 | 7/1989 | Packard et al. . |
| 4,885,204 | 12/1989 | Bither et al. . |
| 4,886,697 | 12/1989 | Perdelwitz et al. . |
| 4,900,377 | 2/1990 | Redford et al. . |
| 4,950,264 | 8/1990 | Osborn . |
| 4,980,226 | 12/1990 | Hellgren et al. . |
| 4,994,037 | 2/1991 | Bernardin . |
| 5,009,650 | 4/1991 | Bernardin . |
| 5,009,653 | 4/1991 | Osborn . |
| 5,025,504 | 6/1991 | Benston et al. . |
| 5,030,500 | 7/1991 | Perdelwitz et al. . |
| 5,045,322 | 9/1991 | Blank et al. ............................ 604/358 |
| 5,085,914 | 2/1992 | Perdelwitz et al. . |
| 5,128,082 | 7/1992 | Makoui . |
| 5,135,521 | 8/1992 | Luceri et al. . |
| 5,139,861 | 8/1992 | Williams et al. . |
| 5,143,779 | 9/1992 | Newkirk et al. . |
| 5,147,345 | 9/1992 | Young et al. . |
| 5,154,714 | 8/1992 | Nomura et al. . |
| 5,160,331 | 11/1992 | Forester et al. . |
| 5,167,764 | 12/1992 | Nielsen et al. . |
| 5,167,765 | 12/1992 | Nielsen et al. . |
| 5,176,668 | 1/1993 | Bernardin . |
| 5,188,624 | 2/1993 | Young, Sr. et al. .................... 604/368 |
| 5,231,122 | 7/1993 | Palumbo et al. . |
| 5,350,370 | 9/1994 | Jackson et al. . |

CATAMENIAL ABSORBENT STRUCTURES HAVING THERMALLY BONDED LAYERS FOR IMPROVED HANDLING OF MENSTRUAL FLUIDS, AND THEIR USE IN CATAMENIAL PADS HAVING IMPROVED FIT AND COMFORT

This is a continuation of application Ser. No. 08/141,156, filed on Oct. 21, 1993 now abandoned.

TECHNICAL FIELD

This application relates to absorbent structures that have thermally bonded fibrous layers for improved handling of bodily fluids, particularly menses. This application also relates to absorbent cores having thermally bonded fibrous layers for efficiently distributing acquired menstrual fluids to a high concentration of absorbent gelling material. This application further relates to catamenial pads (e.g., sanitary napkins), embodying these absorbent structures that not only provide improved fluid handling, but also improved fit and comfort during use.

BACKGROUND OF THE INVENTION

In the case of catamenial pads, women have come to expect a high level of performance in terms of comfort and fit, retention of fluid, and minimal staining. Above all, leakage of fluid from the pad onto undergarments is regarded as totally unacceptable. Improving the performance of such catamenial pads continues to be a formidable undertaking, although a number of improvements have been made in both catamenial structures, and materials used in such structures. However, eliminating leakage, particularly along the inside of the thighs, without compromising fit and comfort, has not always met the desired needs of the consumer.

Leakage from catamenial pads, and in particular sanitary napkins, is generally attributed to a high concentration of fluid at the point where the menses exits the body and immediately contacts the surface of the napkin. At this point of deposit, the napkin absorbent structure can become quickly supersaturated. The blood migrates radially from this point and leaks from the sides nearest the wearer's legs.

This leakage problem for catamenial pads generally, and sanitary napkins in particular, is especially acute for thinner versions of such products. Thinness is a highly desired characteristic in such products. For example, thinner sanitary napkin products are less bulky to wear, fit better under clothing and are less noticeable. Thinner sanitary napkins are also more compact in the package, making them easier to carry and store.

The users of sanitary napkins, and the like, have also come to expect the surface of such products to provide a cleaner, more sanitary and drier aspect than common cloth or nonwoven materials have historically provided. Current sanitary napkin products are typically provided with nonwoven or formed-film permeable topsheets that are designed to move discharged menstrual fluids rapidly therethrough and into an underlying absorbent structure. This rapid movement of acquired menstrual fluids is designed to provide a drier and cleaner surface adjacent the wearer of the product.

The absorbent structures of current catamenial (e.g., sanitary napkin) pads have typically comprised one or more fibrous layers for acquiring the discharged menstrual fluid from the permeable topsheet and distributing it to an underlying storage area. Absorbent structures for relatively thin versions of prior catamenial products usually comprise a fluid acquisition layer (often called a "secondary topsheet") that is adjacent to the permeable topsheet This "secondary topsheet" typically is made from an air-laid-tissue web or a synthetic nonwoven. Underlying this secondary topsheet is the main absorbent core that is typically made from air-laid or wet-laid tissue. The absorbent core often contains a particulate absorbent gelling material that can be encased or enveloped within this tissue. Such encased or enveloped cores are often referred to as tissue laminate cores. See, for example, U.S. Pat. No. 4,950,264 (Osborn), issued Aug. 21, 1990 and U.S. Pat. No. 5,009,653 (Osborn), issued Apr. 23, 1991, that disclose tissue laminate cores used in sanitary napkin products.

The "secondary topsheet" in these prior catamenial absorbent structures is supposed to rapidly draw discharged menstrual fluid through the permeable topsheet so that the surface adjacent the wearer of the article remains relatively clean and dry. The menstrual fluid acquired by the "secondary topsheet" is then distributed to the underlying absorbent core for distribution to the absorbent gelling material for ultimate storage. Unfortunately, the "secondary topsheet" in these prior catamenial absorbent structures tends to collapse when wetted and compressed during use. The fibrous portion of the underlying absorbent core also tends to be dimensionally unstable when wetted (i.e., can either expand or collapse), thus changing its density and pore size distribution. This makes it more difficult to rapidly and adequately transfer menstrual fluid to the absorbent gelling material for storage, especially in "gush" situations. When wetted, the fibrous portion of the absorbent core also become less stiff (due to the elimination of hydrogen bonding between the fibers). Collapse and consolidation of the fibrous portion of the core also results in the product bunching during use.

As a result of these changes that occur during use, prior catamenial absorbent structures have a number of problems. One is the difficulty in insuring adequate topsheet dryness. In particular, the acquired menstrual fluid can potentially leak back through the main topsheet. This phenomenon is often referred to as "rewet." This potential for "rewet" increases as the absorbent structure becomes super saturated with acquired menstrual fluid.

Another problem of prior catamenial absorbent structures is a lower total fluid capacity. Basically, this means only so much of the absorbent gelling material in the absorbent core is effectively utilized to absorb menstrual fluid. The remaining absorbent gelling material a is either underutilized or is not utilized at all. Under utilization is a particular problem for absorbent cores, such as tissue laminates, having high concentration of absorbent gelling material.

These prior catamenial absorbent structures, and in particular catamenial pads using such structures, have had a greater chance of causing panty and body soiling. This is because the absorbent structure lacks resilience, leading to bunching of the pad. This lack of resilience, and consequent bunching, has also caused these prior catamenial pads to provide poorer fit and comfort for the user.

Accordingly, it would be desirable to provide catamenial absorbent structures, as well as catamenial pads embodying such structures that: (1) improve topsheet dryness, even in "gush" situations; (2) have an increased total fluid capacity and ability to retain absorbed fluids so as to reduce "rewet"; (3) have reduced panty and body soiling; and (4) provide improved fit and comfort for the user.

DISCLOSURE OF THE INVENTION

The present invention relates to catamenial absorbent structures for catamenial products, in particular catamenial pads, that are capable of acquiring, distributing and storing aqueous body fluids, especially menstrual fluids, as well as providing better fit and comfort for the user of the products. These absorbent structures comprise:

(A). a fluid acquisition layer (i.e., secondary topsheet) comprising a mixture of hydrophilic cellulosic fibers and thermoplastic material bonding the fibers together into a thermally bonded matrix providing vertical wicking of from about 1 to about 6 cm of artificial menstrual fluid;

(B) a fluid distribution layer in fluid communication with, and being capable of acquiring fluid from, this acquisition layer, the distribution layer comprising a mixture of hydrophilic cellulosic fibers and thermoplastic material bonding these fibers together into a thermally bonded matrix providing vertical wicking of from about 8 to about 20 cm of artificial menstrual fluid;

(C) a fluid storage layer in fluid communication with the distribution layer and comprising from about 15 to 100% absorbent gelling material and from 0 to about 85% of a carrier for the absorbent gelling material;

(D) optionally a fibrous ("dusting") layer adjacent this storage layer comprising a mixture of hydrophilic cellulosic fibers and thermoplastic material bonding these fibers together into a thermally bonded matrix.

The present invention also relates to absorbent cores capable of efficiently distributing and storing such aqueous body fluids, especially menstrual fluids. These absorbent cores comprise:

(A) a primary fluid distribution layer comprising a mixture of hydrophilic cellulosic fibers and thermoplastic material bonding these fibers together into a thermally bonded matrix providing vertical wicking of from about 8 to about 20 cm of artificial menstrual fluid;

(B) a secondary fluid distribution layer in fluid communication with, and being capable of acquiring aqueous body fluids from, the primary distribution layer, this secondary distribution layer comprising a mixture of hydrophilic cellulosic fibers and thermoplastic material bonding these fibers together into a thermally bonded matrix providing vertical wicking of from about 1 to about 6 cm of artificial menstrual fluid;

(C) optionally, but preferably, a fluid storage layer in fluid communication with the secondary distribution layer and comprising from about 15 to 100% absorbent gelling material and from 0 to about 85% of a carrier for the absorbent gelling material;

(D) optionally a fibrous ("dusting") layer adjacent the storage layer and comprising a mixture of hydrophilic cellulosic fibers and thermoplastic material bonding these fibers together into a thermally bonded matrix providing vertical wicking of from about 1 to about 10 cm of artificial menstrual fluid.

The present invention further relates catamenial pads, in particular sanitary napkins that are capable of not only acquiring, distributing and storing aqueous body fluids, especially menstrual fluids, but also provide better fit and comfort for the user of such products. These catamenial pads comprise:

(A) a fluid pervious topsheet selected from apertured formed film topsheets and high loft nonwoven topsheets;

(B). optionally, but preferably, a fluid acquisition layer ("secondary topsheet") adjacent the primary topsheet, the acquisition layer comprising a mixture of hydrophilic cellulosic fibers and thermoplastic material bonding the fibers together into a thermally bonded matrix providing vertical wicking of from about 1 to about 6 cm of artificial menstrual fluid;

(C) an absorbent core in fluid communication with the primary topsheet or the fluid acquisition layer and having:

(1) a primary fluid distribution layer comprising a mixture of hydrophilic cellulosic fibers and thermoplastic material bonding these fibers together into a thermally bonded matrix providing vertical wicking of from about 8 to about 20 cm of artificial menstrual fluid;

(2) optionally, but preferably, a secondary fluid distribution layer in fluid communication with, and being capable of acquiring aqueous body fluids from, the primary distribution layer, this secondary distribution layer comprising a mixture of hydrophilic cellulosic fibers and thermoplastic material bonding these fibers together into a thermally bonded matrix providing vertical wicking of from about 1 to about 6 cm of artificial menstrual fluid;

(3) a fluid storage layer in fluid communication with the primary or secondary distribution layer, and comprising from about 15 to 100% absorbent gelling material and from 0 to about 85% of a carrier for the absorbent gelling material;

(4) optionally a fibrous (dusting) layer adjacent the storage layer and comprising a mixture of hydrophilic cellulosic fibers and thermoplastic material bonding these fibers together into a material bonding these fibers together into a thermally bonded matrix;

(D) a fluid impervious backsheet.

These catamenial pads are further characterized by: (a) compressive force values in the dry state of about 300 g or less; (b) an absolute recovery from compression value in the wet state of at least about 48 mm; and (c) a relative recovery from compression value in the wet state of at least about 65% of the initial pad width.

The absorbent structures and absorbent cores of the present invention offer a number of significant advantages over prior catamenial absorbent structures. These advantages include: (a) improved topsheet dryness, even in "gush" situations; (b) the ability to increase total fluid capacity and retain the absorbed fluid, i.e., reduce "rewet", by increasing the amount of utilized absorbent gelling material; and (c) reduced panty and body soiling because of the improved flexibility and resiliency of the thermally bonded materials used, even when wetted and compressed during use. Moreover, catamenial pads, such as sanitary napkins embodying these absorbent cores and structures not only provide improved fluid handling, but also improved fit and comfort for user, especially in terms of preventing bunching of the pads during use.

DETAILED DESCRIPTION OF INVENTION

A. Definitions

Figure 1:
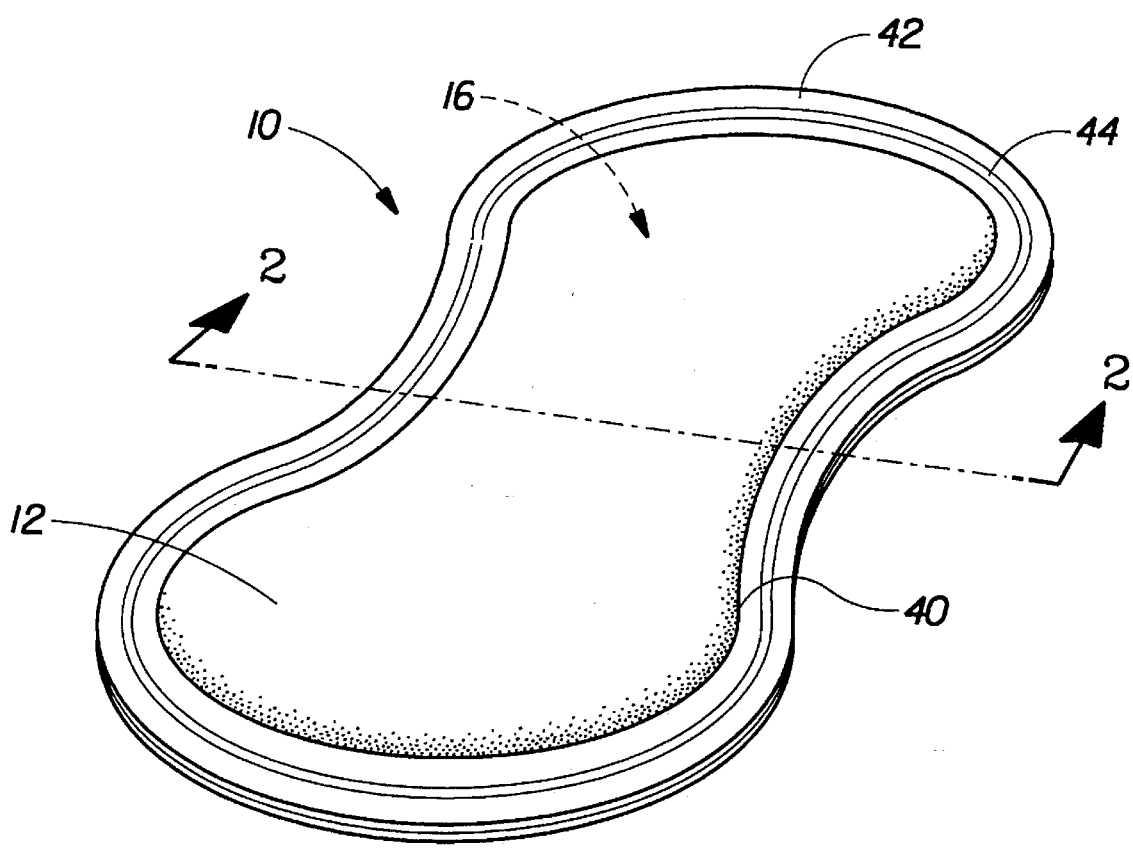
FIG. 1 is perspective view of a catamenial product having absorbent structures according to the present invention.

As used herein, the term "aqueous body fluids" includes urine, menses and vaginal discharges.

As used herein, the term "Z-dimension" refers to the dimension orthogonal to the length and width of the layer, structure or article. The Z-dimension usually corresponds to the thickness of the layer, structure or article.

As used herein, the term "X-Y dimension" refers to the plane orthogonal to the thickness of the layer, structure or article. The X-Y dimension usually corresponds to the length and width of the layer, structure or article.

As used herein, the term "comprising" means various components, layers, structures, articles, steps and the like can be conjointly employed according to the present invention. Accordingly, the term "comprising" encompasses the more restrictive terms "consisting essentially of" and "consisting of," these latter, more restrictive terms having their standard meaning as understood in the art.

All percentages, ratios and proportions used herein are by weight unless otherwise specified.

B. Composition of Secondary Topsheet and Other Thermally Bonded Layers

The secondary topsheet, as well as the other thermally bonded layers of the absorbent cores and structures of the present invention comprise the following components:

1. Hydrophilic Cellulosic Fibers

The secondary topsheet and other thermally bonded layers according to the present invention comprise a fibrous web or matrix of hydrophilic cellulosic fibers. This fibrous web or matrix provides the primary medium for handling aqueous fluids and in particular discharged aqueous body fluids, such as menses. This web or matrix typically provides a capillary structure for handling such fluids. Such fluid handling includes acquisition of the initially discharged fluid, transportation and distribution of this acquired fluid to other remote regions of the web or matrix, as well as storage of this acquired fluid.

Hydrophilic cellulosic fibers useful in the present invention include naturally occurring, unmodified cellulosic fibers, as well as modified cellulosic fibers. Examples of suitable unmodified/modified cellulosic fibers include cotton, Esparto grass, bagasse, kemp, flax, wood pulp, chemically modified wood pulp, jute, rayon, and the like. The fibrous web or matrix can comprise solely unmodified cellulosic fibers, solely modified cellulosic fibers, or any compatible combination of unmodified and modified cellulosic fibers.

The cellulosic fibers used in the present invention are hydrophilic. As used herein, the term "hydrophilic" describes fibers, or surfaces of fibers, that are wettable by aqueous fluids (e.g., aqueous body fluids) deposited on these fibers. Hydrophilicity and wettability are typically defined in terms of contact angle and the surface tension of the fluids and solids involved. This is discussed in detail in the American Chemical Society publication entitled *Contact Angle, Wettability and Adhesion,* edited by Robert F. Gould (Copyright 1964). A fiber, or surface of a fiber, is said to be wetted by a fluid (i.e., hydrophilic) when either the contact angle between the fluid and the fiber, or its surface, is less than 90°, or when the fluid tends to spread spontaneously across the surface of the fiber, both conditions normally co-existing. Conversely, a fiber or surface is considered to be hydrophobic if the contact angle is greater than 90° and the fluid does not spread spontaneously across the surface of the fiber.

For reasons of availability and cost, wood pulp fibers are preferred cellulosic fibers for use in the present invention. Suitable wood pulp fibers can be obtained from well-known chemical processes such as the Kraft and sulfite processes. It is especially preferred to derive these wood pulp fibers from southern soft woods due to their premium absorbency characteristics. These wood pulp fibers can also be obtained from mechanical processes, such as ground wood, refiner mechanical, thermomechanical, chemimechanical, and chemithermomechanical pulp processes. Recycled or secondary wood pulp fibers, as well as bleached and unbleached wood pulp fibers, can be used.

Hydrophilic cellulosic fibers useful in the present invention include chemically stiffened cellulosic fibers. As used herein, the term "chemically stiffened cellulosic fibers" means cellulosic fibers that have been stiffened by chemical means to increase the stiffness of the fibers under both dry and aqueous conditions. Such means can include the addition of a chemical stiffening agent that, for example, coats and/or impregnates the fibers. Such means can also include the stiffening of the fibers by altering the chemical structure, e.g., by crosslinking polymer chains.

Polymeric stiffening agents that can coat or impregnate the cellulosic fibers include: cationic modified starches having nitrogen-containing groups (e.g., amino groups) such as those available from National Starch and Chemical Corp., Bridgewater, N.J., USA; latexes; wet strength resins such as polyamideepichlorohydrin resin (e.g., Kymene® 557H, Hercules, Inc. Wilmington, Del., USA), polyacrylamide resins described, for example, in U.S. Pat. No. 3,556,932 (Coscia et al), issued Jan. 19, 1971; commercially available polyacrylamides marketed by American Cyanamid Co., Stamford, Conn., USA, under the tradename Parez® 631 NC; urea formaldehyde and melamine formaldehyde resins, and polyethylenimine resins. A general dissertation on wet strength resins utilized in the paper art, and generally applicable herein, can be found in TAPPI monograph series No. 29. "Wet Strength in Paper and Paperboard", Technical Association of the Pulp and Paper Industry (New York, 1965).

These fibers can also be stiffened by chemical reaction. For example, crosslinking agents can be applied to the fibers that, subsequent to application, are caused to chemically form intrafiber crosslink bonds. These crosslink bonds can increase the stiffness of the fibers. While the utilization of intrafiber crosslink bonds to chemically stiffen the fibers is preferred, it is not meant to exclude other types of reactions for chemical stiffening of the fibers.

Fibers stiffened by crosslink bonds in individualized form (i.e., the individualized stiffened fibers, as well as processes for their preparation) are disclosed, for example, in U.S. Pat. No. 3,224,926 (Bernardin), issued Dec. 21, 1965; U.S. Pat. No. 3,440,135 (Chung), issued Apr. 22, 1969; U.S. Pat. No. 3,932,209 (Chatterjee), issued Jan. 13, 1976; and U.S. Pat. No. 4,035,147 (Sangenis et al.), issued Jul. 12, 1977. More preferred stiffened fibers are disclosed in U.S. Pat. No. 4,822,453 (Dean et al), issued Apr. 18, 1989; U.S. Pat. No. 4,888,093 (Dean et al), issued Dec. 19, 1989; U.S. Pat. No. 4,898,642 (Moore et al), issued Feb. 6, 1990; and U.S. Pat. No. 5,137,537 (Herron et al), issued Aug. 11, 1992, all of which are incorporated by reference.

In the more preferred stiffened fibers, chemical processing includes intrafiber crosslinking with crosslinking agents while such fibers are in a relatively dehydrated, defibrated (i.e., individualized), twisted, curled condition. Suitable chemical stiffening agents are typically monomeric crosslinking agents including, but not limited to, $C_2$–$C_8$ dialdehyde, $C_2$–$C_8$ monoaldehydes having an acid functionality, and especially $C_2$–$C_9$ polycarboxylic acids. These compounds are capable of reacting with at least two hydroxyl groups in a single cellulose chain or on proximately located cellulose chains in a single fiber. Specific examples of such crosslinking agents include, but are not limited to, glutaraldehyde, glyoxal, formaldehyde, glyoxylic acid, oxydisuccinic acid and citric acid. The effect of crosslinking under these conditions is to form fibers that are stiffened and which tend to retain their twisted, curled configuration during use in the thermally bonded absorbent structures herein. Such fibers, and processes for making them, are described in the above incorporated patents.

The preferred stiffened fibers that are twisted and curled can be quantified by referencing both a fiber "twist count" and a fiber "curl factor". As used herein, the term "twist count" refers to the number of twist nodes present in a certain length of fiber. Twist count is utilized as a means of measuring the degree to which a fiber is rotated about its longitudinal axis. The term "twist node" refers to a substantially axial rotation of 180° about the longitudinal axis of the fiber, wherein a portion of the fiber (i.e., the "node") appears dark relative to the rest of the fiber when viewed under a microscope with transmitted light. The twist node appears dark at locations wherein the transmitted light passes through an additional fiber wall due to the aforementioned rotation. The distance between nodes corresponds to an axial rotation of 180°. The number of twist nodes in a certain length of fibers (i.e., the twist count) is directly indicative of the degree of fiber twist, which is a physical parameter of the fiber. The procedures for determining twist nodes and total twist count are described in U.S. Pat. No. 4,898,642.

The preferred stiffened fibers will have an average dry fiber twist count of at least about 2.7, preferably at least about 4.5 twist, nodes per millimeter. Furthermore, the average wet fiber twist count of these fibers should preferably be at least about 1.8, preferably at least about 3.0, and should also preferably be at least about 0.5 twist nodes per millimeter less than the average dry fiber twist count. Even more preferably, the average dry fiber twist count should be at least about 5.5 twist nodes per millimeter, and the average wet fiber twist count should be at least about 4.0 twist nodes per millimeter and should also be at least 1.0 twist nodes per millimeter less than its average dry fiber twist count. Most preferably, the average dry fiber twist count should be at least about 6.5 twist nodes per millimeter, and the average wet fiber twist count should be at least about 5.0 twist nodes per millimeter and should also be at least 1.0 twist nodes per millimeter less than the average dry fiber twist count.

In addition to being twisted, these preferred stiffened fibers are also curled. Fiber curl can be described as the fractional shortening of the fiber due to kinks, twists, and/or bends in the fiber. For the purposes of the present invention, fiber curl is measured in terms of a two dimensional plane. The extent of fiber curling can be quantified by referencing a fiber curl factor. The fiber curl factor, a two dimensional measurement of curl, is determined by viewing the fiber in a two dimensional plane. To determine curl factor, the projected length of the fiber as the longest dimension of a two dimensional rectangle encompassing the fiber, $L_R$, and the actual length of the fiber, $L_A$, are both measured. The fiber curl factor can then be calculated from the following equation:

$$\text{Curl Factor} = (L_A/L_R) - 1.$$

An image analysis method that can be utilized to measure $L_R$ and $L_A$ is described in U.S. Pat. No. 4,898,642. Preferably the stiffened fibers will have a curl factor of at least about 0.30, and more preferably will have a curl factor of at least about 0.50.

2. Thermoplastic Material

In addition to the hydrophilic cellulosic fibers, the secondary topsheet and other thermally bonded layers according to the present invention comprise thermoplastic material. Upon melting, at least a portion of this thermoplastic material migrates to the intersections of the fibers, typically due to interfiber capillary gradients. These intersections become bond sites for the thermoplastic material. When cooled, the thermoplastic material at these intersections solidify to form the bond sites that hold the web or matrix of fibers.

Amongst its various effects, bonding at these fiber intersections increases the overall compressive modulus and strength of the resulting thermally bonded matrix. In the case of the chemically stiffened cellulosic fibers, the melting and migration of the thermoplastic material also has the effect of increasing the average pore size of the resultant web, while maintaining the density and basis weight of the web as originally formed. This can improve the fluid acquisition properties of the thermally bonded layer (e.g., secondary topsheet) upon initial discharges, due to improved fluid permeability, and upon subsequent discharges, due to the combined ability of the stiffened fibers to retain their stiffness upon wetting and the ability of the thermoplastic material to remain bonded at the fiber intersections upon wetting and upon wet compression. In net, thermally bonded webs of stiffened fibers retain their original overall volume, but with the volumetric regions previously occupied by the thermoplastic material becoming open to thus increase the average interfiber capillary pore size.

Thermoplastic materials useful in the present invention can be in any of a variety of forms including particulates, fibers, or combinations of particulates and fibers. Thermoplastic fibers are a particularly preferred form because of their ability to form numerous interfiber bond sites. Suitable thermoplastic materials can be made from any thermoplastic polymer that can be melted at temperatures that will not extensively damage the fibers that comprise the primary web or matrix of each layer. Preferably, the melting point of this thermoplastic material will be less than about 190° C., and preferably between about 75° C. and about 175° C. In any event, the melting point of this thermoplastic material should be no lower than the temperature at which the thermally bonded absorbent structures, when used in absorbent articles, are likely to be stored. The melting point of the thermoplastic material is typically no lower than about 50° C.

The thermoplastic materials, and in particular the thermoplastic fibers, can be made from a variety of thermoplastic polymers, including polyolefins such as polyethylene (e.g., PULPEX®) and polypropylene, polyesters, copolyesters, polyvinyl acetate, polyethylvinyl acetate, polyvinyl chloride, polyvinylidene chloride, polyacrylics, polyamides, copolyamides, polystyrenes, polyurethanes and copolymers of any of the foregoing such as vinyl chloride/vinyl acetate, and the like. One preferred thermoplastic binder fiber is PLEXAFIL® polyethylene microfibers (made by DuPont) that are also available as an about 20% blend with 80% cellulosic fibers sold under the tradename KITTYHAWK® (made by Weyerhaeuser Co.). Depending upon the desired characteristics for the resulting thermally bonded matrix, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, polyurethanes and the like. The surface of the hydrophobic thermoplastic fiber can be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij 76 manufactured by ICI Americas, Inc. of Wilmington, Del., and various surfactants sold under the Pegosperse® trademark by Glyco Chemical, Inc. of Greenwich, Conn. Besides nonionic surfactants, anionic surfactants can also be used. These surfactants can be applied to the thermoplastic fibers at levels of, for example, from about 0.2 to about 1 g. per sq. of centimeter of thermoplastic fiber.

Suitable thermoplastic fibers can be made from a single polymer (monocomponent fibers), or can be made from more than one polymer (e.g., bicomponent fibers). As used herein, the term "bicomponent fibers" refers to thermoplastic fibers that comprise a core fiber made-from one polymer that is encased within a thermoplastic sheath made from a different polymer. The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention can include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CELBOND® or CHISSO® bicomponent fibers). These bicomponent fibers can be concentric or eccentric. As used herein, the terms "concentric" and "eccentric" refer to whether the sheath has a thickness that is even, or uneven, through the cross-sectional area of the bicomponent fiber. Eccentric bicomponent fibers can be desirable in providing more compressive strength at lower fiber thicknesses. Suitable bicomponent fibers for use herein can be either uncrimped (i.e. unbent) or crimped (i.e. bent). Bicomponent fibers can be crimped by typical textile means such as, for example, a stuffer box method or the gear crimp method to achieve a predominantly two-dimensional or "flat" crimp.

In the case of bicomponent thermoplastic fibers, their length can vary depending upon the particular properties desired for these fibers. Typically, these thermoplastic fibers have a length from about 0.3 to about 7.5 cm long, preferably from about 0.4 to about 3.0 cm long, and most preferably from about 0.6 to about 1.2 cm long. The properties-of these thermoplastic fibers can also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers can have a decitex in the range from about 1.0 to about 20, preferably from about 1.4 to about 10, and most preferably from about 1.7 to about 3.3.

The compressive modulus of these thermoplastic materials, and especially that of the thermoplastic fibers, can also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers can be used to alter the properties, and especially the density characteristics, of the respective thermally bonded fibrous matrix.

3. Optional Synthetic Fibers

The secondary topsheet and other thermally bonded layers according to the present invention can optionally comprise some synthetic fibers that typically do not function as binder fibers but alter the mechanical properties of the fibrous webs. Suitable synthetic fibers for use in the present invention include polyester fibers such as polyethylene terephthalate (e.g., DACRON® and KODEL®), high melting crimped polyester fibers (e.g., KODEL® 431 made by Eastman Chemical Co.) hydrophilic nylon (HYDROFIL®), and the like. Suitable fibers can also hydrophilized hydrophobic fibers, such as surfactant-treated or silica-treated thermoplastic fibers derived from, for example, polyolefins such as polyethylene or polypropylene, polyacrylics, polyamides, polystyrenes, polyurethanes and the like. In the case of nonbonding thermoplastic fibers, their length can vary depending upon the particular properties desired for these fibers. Typically they have a length from about 0.3 to 7.5 cm, preferably from about 0.9 to about 1.5 cm. Suitable nonbonding thermoplastic fibers can have a decitex in the range of about 1.5 to about 35 decitex, more preferably from about 14 to about 20 decitex.

4. Preparation or Secondary Topsheet and Other Thermally Bonded Layers
   a. Forming Layers from Mixtures of Fibers and Thermoplastic Material The thermally bonded secondary topsheet, as well as the other thermally bonded layers of the absorbent core, are formed from a mixture of hydrophilic cellulosic fibers and thermoplastic material previously described, plus any optional components such as hydrophilic synthetic fibers. The thermoplastic material is typically evenly distributed throughout the web or matrix of fibers in each layer, i.e. the composition of each fibrous layer is substantially homogeneous. This not only assures adequate interfiber bonding of this fibrous web/matrix, but also insures that the resulting fibrous layer has a substantially uniform density when subjected to subsequent thermal bonding and densification.

The particular amount of cellulosic fibers and thermoplastic material within this mixture for each layer depends upon a number of factors, including the degree of thermal bonding desired, the particular fibers and thermoplastic material used, the particular density or other properties desired for the resulting thermally bonded layer, and like factors. Typically, this mixture comprises from about 10 to about 95% cellulosic fibers and from about 5 to about 90% thermoplastic material. Preferably, this mixture comprises from about 55 to about 90% fibers and from about 10 to about 45% thermoplastic material, most preferably from about 70 to 90% cellulosic fibers and from about 10 to about 30% thermoplastic material.

The mixtures of fibers and thermoplastic material can be formed into layers by any of a variety of techniques, including wet-laying methods and air-laying methods. Techniques for wet-laying cellulosic fibrous material to form paper are well known in the art. These techniques are generally applicable to the wet-laying of mixtures of fibers, especially cellulosic fibers, and thermoplastic material, especially thermoplastic fibers, to form wet-laid absorbent structures according to the present invention. Suitable wet-laying techniques include hand sheeting, and wet-laying by utilizing paper-making machines, as disclosed, for example, in U.S. Pat. No. 3,301,746 (Sanford et al), issued Jan. 31, 1967. In general, wet-laid fibrous webs are made by depositing an aqueous slurry of fibers and thermoplastic material from a headbox onto a foraminous forming wire, dewatering the wet-laid slurry to form a wet web, and then drying this wet web. Wet-laid paper-making processes involving the deposit of two or more aqueous slurries of fibers to form two or more paper webs that are ultimately combined to form a unitary, layered web are particularly suitable for forming wet-laid absorbent structures according to the present invention. In this regard, the process disclosed in U.S. Pat. No. 3,994,771 (Morgan et al), issued Nov. 30, 1967 (herein incorporated by reference), for forming layered paper webs is suitable for forming wet-laid absorbent structures according to the present invention.

In wet-laying mixtures that include chemically stiffened cellulosic fibers, special techniques for depositing the aqueous slurry of stiffened fibers and thermoplastic material can be required. These stiffened fibers have the tendency to flocculate, or form clumps, in aqueous solution. In order to inhibit this flocculation, aqueous slurries of stiffened fibers and thermoplastic material should be pumped to the headbox from which they are deposited at a linear velocity of at least about 0.25 meters/second. It is also preferred that the linear velocity of these slurries upon exit from the headbox be from about 2.0 to about 4.0×the velocity of the forming wire. Another method for reducing flocculation of these chemically stiffened fibers in a wet-laying process is described in U.S. Pat. No. 4,889,597 (Bourbon et al), issued Dec. 27, 1989 (herein incorporated by reference) where jets of water are directed at the wet-laid stiffened fibers just after deposition on the forming wire.

More typically, each fibrous layer of the absorbent structure according to the present invention is formed by air-laying the mixture of fibers and thermoplastic material. In general, air-laying can be carried out by metering an airflow containing the fibers and thermoplastic material, in substantially dry condition, onto a typically horizontally moving wire forming screen. Suitable systems and apparatus for air-laying mixtures of fibers and thermoplastic material are disclosed in, for example, U.S. Pat. No. 4,157,724 (Persson), issued Jun. 12, 1979, and reissued Dec. 25, 1984 as Re. 31,775; U.S. Pat. No. 4,278,113 (Persson), issued Jul. 14, 1981; U.S. Pat. No. 4,264,289 (Day), issued Apr. 28, 1981; U.S. Pat. No. 4,352,649 (Jacobsen et al), issued Oct. 5, 1982; U.S. Pat. No. 4,353,687 (Hosler et al), issued Oct. 12, 1982; U.S. Pat. No. 4,494,278 (Kroyer et al), issued Jan. 22, 1985; U.S. Pat. No. 4,627,806 (Johnson), issued Dec. 9, 1986; U.S. Pat. No. 4,650,409 (Nistri et al), issued Mar. 17, 1987; and U.S. Pat. No. 4,724,980 (Farley), issued Feb. 16, 1988, all of which are incorporated by reference.

A particularly desirable system for air-laying mixtures of fibers and thermoplastic material according to the present invention is disclosed in U.S. Pat. No. 4,640,810 (Laursen et al), issued Feb. 3, 1987, which is incorporated by reference. In this system, the fibers and thermoplastic material are blended, and while supported in an airstream, are introduced into a distributor unit. This distributor unit includes one or more rotatable cylindrical drums formed with classification apertures of predetermined shape, number and size as specifically related to the types of fibers and thermoplastic material utilized. To accept flows of relatively short fibers, or thermoplastic material in particulate form, these apertures are preferably circular and have a diameter substantially equivalent to the length or size of the fibers and/or particles introduced into the system, and are large in number per unit length of the drum. To accept flows of relatively long fibers, or blends of long and short fibers and/or particles, these apertures are preferably rectangular in configuration with a length generally twice that of the long fibers and a width generally ten times the diameter of these fibers. Because the rectangular apertures are larger than the circular apertures, their number is moderate per length of the drum in comparison to the circular apertures.

Each of the cylindrical drums has within it a shaft with radially extending wire-like members that is rotated in a direction opposite that of the associated drum. The wire-like members engage the individual fibers and/or particles and fling them through the apertures in the drum. Simultaneously, the wire-like members agitate the fibers and/or particles to maintain a homogeneous mixture thereof. A downwardly directed airflow then transports this homogeneous-airborne mixture onto a typically horizontally moving foraminous carrier so as to form a layer of fibers and/or particles of substantially uniform composition.

The respective mixtures of hydrophilic cellulosic fibers and thermoplastic material for the secondary topsheet and other layers of the absorbent structure can be formed separately and then combined later after thermal bonding/densification. Alternatively, if an integral absorbent structure is desired, the secondary topsheet, as well as one or more of the other layers in the absorbent structure can be formed at the same time. In forming those these integral thermally bonded absorbent structures, one of the fibrous layers is formed comprising the mixture of fibers and thermoplastic material. The subsequent fibrous layers are also formed and then combined with the first layer. It should be understood that the formation of the respective layers and their combination could occur in any order and in any number of orientations, including horizontal and vertical planes. In particular, it should be understood that formation of the first fibrous layer need not be completed prior to the start of formation of the subsequent fibrous layers. Indeed, the first fibrous layer need only be partially formed prior to the start of formation of the subsequent fibrous layers. Typically, the subsequent fibrous layers are formed by depositing them on top of a complete, or only partially formed, first fibrous layer that is oriented horizontally.

b. Thermal Bonding and Densification of Combined Layers

After the fibrous layer, or in the case of integral absorbent structures, layers are formed, they are thermally bonded and then typically densified. Thermal bonding and densification of the fibrous layer or layers can occur in a number of different orders. For example, densification of the fibrous layer(s) can occur prior to thermal bonding, during thermal bonding and/or after thermal bonding. The particular order in which these densification and thermal bonding steps occur will often depend upon the particular fibers and thermoplastic material present in the respective fibrous layer(s), the particular properties desired in the resulting thermally bonded layer(s), especially the particular density characteristic desired, and like factors.

Densification of the fibrous layer(s) is usually carried out by the application of pressure. For example, in the case of wet-laid layers, at least some densification can occur during the dewatering of the wet-laid fibrous layers. In the case of air-laid layers, compressive forces are typically applied to the opposed surfaces of the layer. Such compressive forces can be applied by using opposed platens, or more typically by the use or opposed rollers. Preferably, a pair of opposed calender rolls are used to apply compressive forces to the air-laid layer(s).

Thermal bonding of the formed layer(s) can be carried out by any of a variety of techniques. For example, in the case of wet-laid layers, at least some thermal bonding can occur during thermal drying of the wet-laid fibrous layers. In the case of air-laid layers, thermal bonding is typically achieved by heating the formed layer(s) above the melt point of the thermoplastic material present therein. Air-laid layers are typically heated to temperatures in the range from about 70° to about 190° C., preferably from about 100° to about 160° C., and most preferably from about 120° to about 150° C. The particular temperature to which the layer is heated will depend upon a number of factors, including the melt point of the thermoplastic material present in the fibrous layer, the particular properties desired in the resulting thermally bonded fibrous matrix, and like factors.

The formed layer(s) can be heated by any of a variety of techniques. One such technique involves heating the formed layer(s) while it is being subjected to compressive forces required for densification. For example, the formed layer(s) can be passed between a pair of opposed calender rolls, one or both of which have been heated to the appropriate temperature. A particularly suitable technique for heating air-laid layers is by passing them through a hot-air oven in the absence of the application of compressive forces.

C. Absorbent Structure Components

1. Secondary Topsheet

Absorbent structures according to the present invention typically include a fluid acquisition layer. This fluid acquisition layer is commonly referred to in the catamenial art as a "secondary topsheet". The purpose of the secondary topsheet is to rapidly draw discharged aqueous body fluids, in particular menstrual fluids, through the adjacent permeable (primary) topsheet. This allows the surface of the primary topsheet adjacent the wearer of the catamenial pad to remain relatively clean and dry.

2. Absorbent Core

In addition to the secondary topsheet, absorbent structures according to the present invention comprise an absorbent core. This absorbent core typically includes the following components: (a) a primary fluid distribution layer; (b) optionally, but preferably, a secondary fluid distribution layer; (c) a fluid storage layer; and (d) optionally a fibrous ("dusting") layer underlying the storage layer.

a. Primary Fluid Distribution Layer

A key component of the absorbent cores according to the present invention is the primary fluid distribution layer. This primary distribution layer typically underlies the secondary topsheet and is in fluid communication therewith. The secondary topsheet transfers the acquired menstrual fluid to this primary distribution layer for ultimate distribution to the storage layer. This transfer of fluid through the primary distribution layer occurs not only in the Z-dimension (i.e., its thickness), but also in the X and Y direction (i.e., along its length and width).

b. Optional Secondary Fluid Distribution Layer

An optional, but preferred component of the absorbent cores according to the present invention is a secondary fluid distribution layer. This secondary distribution layer typically underlies the primary distribution layer and is in fluid communication therewith. The purpose of this secondary distribution layer is to readily acquire menstrual fluid from the primary distribution layer and transfer it rapidly to the underlying storage layer. This permits the fluid capacity of the underlying storage layer to be fully utilized. When a secondary distribution layer is included in the absorbent core, the secondary topsheet need not be included in the absorbent structure. However, the inclusion of a secondary topsheet is usually preferred for optimum fluid-handling performance, even when the absorbent core has this secondary distribution layer.

c. Fluid Storage Layer

Positioned in fluid communication with, and typically underlying the primary or secondary distribution layers, is a fluid storage layer comprising certain absorbent gelling materials usually referred to as "hydrogels," "superabsorbent" "hydrocolloid" materials. Absorbent gelling materials are those materials that, upon contact with aqueous fluids, especially aqueous body fluids, imbibes such fluids and thus form hydrogels. These absorbent gelling materials are typically capable of absorbing large quantities of aqueous body fluids, and are further capable of retaining such absorbed fluids under moderate pressures. These absorbent gelling materials are also typically in the form of discrete, nonfibrous particles.

This fluid storage layer can comprise solely absorbent gelling materials, or these absorbent gelling materials can be dispersed in a suitable carrier. Suitable carriers include cellulose fibers, in the form of fluff, such as is conventionally utilized in absorbent cores. Modified cellulose fibers such as the stiffened cellulose fibers described above can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferred synthetic fibers have a denier of from about 3 denier per filament to about 25 denier per filament, more preferably from about 5 denier per filament to about 16 denier per filament. Also preferably, the fiber surfaces are hydrophilic or are treated to be hydrophilic. The storage layer can also include filler materials, such as Perlite, diatomaceous earth, Vermiculite, etc., that lower rewet problems.

Generally, the storage layer comprises from about 15 to 100% absorbent gelling materials and from 0 to about 85% carrier. Preferably, the storage layer comprises from about 30 to 100%, most preferably from about 60 to 100% absorbent gelling materials and from 0 to about 70%, most preferably from 0 to about 40%, carrier.

One of the primary benefits of the absorbent structures of the present invention is the ability to more effectively utilize the absorbent gelling material in this storage layer. Because of gel blocking and poor fluid transport of menses, the level of absorbent gelling material that can be included in prior catamenial absorbent structures is typically about 60 grams per square meter (gsm) or less. By contrast, the absorbent structures according to present invention permit the absorbent gelling material to be effectively utilized at levels at least as high as 120 gsm. By "effectively utilized" is meant that the absorbent gelling material absorbs at least 14 grams of artificial menstrual fluid per gram of absorbent gelling material, as measured by Horizontal Gravimetric Wicking (HGW). See Test Methods section for procedure to measure HGW.

Suitable absorbent gelling materials for use herein will most often comprise a substantially water-insoluble, slightly crosslinked, partially neutralized, polymeric gelling material. This material forms a hydrogel upon contact with water. Such polymer materials can be prepared from polymerizable, unsaturated, acid-containing monomers. Suitable unsaturated acidic monomers for use in preparing the polymeric absorbent gelling material used in this invention include those listed in U.S. Pat. No. 4,654,039 (Brandt et al), issued Mar. 31, 1987, and reissued as RE 32,649 on Apr. 19, 1988, both of which are incorporated by reference. Preferred monomers include acrylic acid, methacrylic acid, and 2-acrylamido-2-methyl propane sulfonic acid. Acrylic acid itself is especially preferred for preparation of the polymeric gelling material. The polymeric component formed from the unsaturated, acid-containing monomers can be grafted onto other types of polymer moieties such as starch or cellulose. Polyacrylate grafted starch materials of this type are especially preferred. Preferred polymeric absorbent gelling materials that can be prepared from conventional types of monomers include hydrolyzed acrylonitrile grafted starch, polyacrylate grafted starch, polyacrylates, maleic anhydride-based copolymers and combinations thereof. Especially preferred are the polyacrylates and polyacrylate grafted starch.

Whatever the nature of the basic polymer components of the hydrogel-forming polymeric absorbent gelling materials, such materials will in general be slightly crosslinked. Crosslinking serves to render the hydrogel-forming polymer gelling materials substantially water-insoluble, and crosslinking thus in part determines the gel volume and extractable polymer characteristics of the hydrogels formed from these polymeric gelling materials. Suitable crosslinking agents are well known in the art and include, for example, those described in greater detail in U.S. Pat. No. 4,076,663 (Masuda et al),; issued Feb. 28, 1978, which is incorporated by reference. Preferred crosslinking agents are the di- or polyesters of unsaturated mono- or polycarboxylic acids with polyols, the bisacrylamides and the di- or triallyl amines. Other preferred crosslinking agents are N,N'-methylenebisacrylamide, trimethylol propane triacrylate and triallyl amine. The crosslinking agent can generally constitute from about 0.001 mole percent to 5 mole percent of the resulting hydrogel-forming polymer material. More preferably, the crosslinking agent will constitute from about 0.01 mole percent to 3 mole percent of the hydrogel-forming polymeric gelling material.

The slightly crosslinked, hydrogel-forming polymeric gelling materials are generally employed in their partially neutralized form. For purposes of the present invention, such materials are considered partially neutralized when at least 25 mole per-cent, and preferably at least 50 mole percent of monomers used to form the polymer are acid group-containing monomers that have been neutralized with a salt-forming cation. Suitable salt-forming cations include alkali metal, ammonium, substituted ammonium and amines. This percentage of the total monomers utilized which are neutralized acid group-containing monomers is referred to herein as the "degree of neutralization."

While these absorbent gelling materials are typically in particle form, it is also contemplated that the absorbent gelling material can be in the form of macrostructures such as fibers, sheets or strips. These macrostructures are typically prepared by forming the particulate absorbent gelling material into an aggregate, treating the aggregated material with a suitable crosslinking agent, compacting the treated aggregate to densify it and form a coherent mass, and then curing the compacted aggregate to cause the crosslinking agent to react with the particulate absorbent gelling material to form a composite, porous absorbent macrostructure. Such porous, absorbent macrostructures are disclosed, for example, in U.S. Pat. No. 5,102,597 (Roe et al), issued Apr. 7, 1992, which is incorporated by reference.

d. Optional Fibrous ("Dusting") Layer

An optional component for inclusion in the absorbent cores according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of macrostructures such as fibers, sheets or strips, this fibrous "dusting" layer need not be included. However, because this "dusting" layer provides some additional fluid-handling capabilities such as rapid wicking of menstrual fluid along the length of the pad, its inclusion is typically preferred in absorbent cores according to the present invention.

e. Other Optional Components

The absorbent cores according to the present invention can include other optional components normally present in absorbent webs. For example, a reinforcing scrim can be positioned within the respective layers, or between the respective layers, of the absorbent cores. Such reinforcing scrims should be of such configuration as to not form interfacial barriers to fluid transfer, especially if positioned between the respective layers of the absorbent core. Given the structural integrity that usually occurs as a result of thermal bonding, reinforcing scrims are usually not required for the absorbent structures according to the present invention.

3. Preferred Thermally Bonded Materials for Secondary Topsheet, Distribution Layers, and Fibrous ("Dusting") Layers, and Methods for Making Same The secondary topsheet, secondary distribution layer and optional "dusting" layer are preferably air laid using an air laying head similar to that disclosed in U.S. Pat. No. 4,640,810 (Laursen et al), issued Feb. 3, 1987, which is incorporated by reference. The fibrous materials are deposited from a single air laying head at a weight of about 20 to about 70 grams per square meter (gsm). A defibrator is used to blend the fibrous materials into an air stream that is fed to the air laying head. After the fibrous materials are laid down and combined to form a web, they go through an oven that melts the outer coating (sheath) of the binding fibers. The oven temperature is typically set so the binding fibers are at a temperature above the melt point of the sheath but below that of the core. The web can be compressed before and/or after the oven to achieve the desired dry and/or wet density. The final web is then cooled to set the bonds between fibers.

Some representative mixtures useful in forming the secondary topsheets and secondary distribution layers include: (1) from about 45 to about 90% (preferably from about 65 to about 85%) wood pulp fibers (preferably Southern Softwood Kraft fibers), up to about 30% (preferably from about 10 to about 20%) hydrophilic nonbonding thermoplastic fibers (preferably high melting crimped polyester KODEL® 431 fibers), and from about 10 to about 50% (preferably from about 10 to about 20%) bicomponent thermoplastic binder fibers (preferably DANAKLON® ES C 3.3 dtex×6 mm crimped bicomponent binder fibers comprising 50% sheath (polyethylene) and 50% core (polypropylene)); and (2) for fibrous "dusting" layers, from about 85 to about 90% wood pulp fibers (preferably 90% Southern Softwood Kraft fibers), and from about 5 to about 15% (preferably 10%) bicomponent thermoplastic binder fibers (preferably DANAKLON® ES C 1.7 dtex×6 mm crimped bicomponent binder fibers).

A particularly preferred mixture for secondary topsheets and secondary distribution layers comprises about 70% Southern Softwood Kraft fibers, about 15% high melting crimped polyester KODEL® 431 fibers, and about 15% DANAKLON® ES C 3.3 dtex×6 mm crimped bicomponent binder fibers. These mixtures are preferably laid at a basis weight in the range of from about 40 to about 60 gsm, and most preferably in the range of from about 45 to about 55 gsm.

The wet caliper, wet density, wet compression, vertically wicking and basis weight properties of a representative thermally bonded material useful as a secondary topsheet in the present invention are shown in Table 1 below:

TABLE 1

| Material | Wet Caliper (mils) | | Wet Density (g/cc) | | % Wet Compression | | Vertical Wicking (cm) | Basis Weight gsm |
|---|---|---|---|---|---|---|---|---|
| | at 0.041 psi | at 0.167 psi | at 0.041 psi | at 0.167 psi | at 0.041 psi | at 0.167 psi | | |
| 1 | 4.36 | 34 | 0.047 | 0.061 | 12.4 | 22.0 | 2.0 | 53 |

The primary fluid distribution layer (with basis weights of from about 50 to about 200 grams per square meter) are produced similarly from the mixture of hydrophilic cellulosic fibers and thermoplastic binding fibers. Optionally, a low level (up to about 20%) of hydrophilic nonbonding thermoplastic fibers can be included. Some representative mixtures include: (1) from about 80 to about 90% wood pulp fibers (preferably Southern Softwood Kraft fibers), and from about 10 to about 20% bicomponent thermoplastic binder fibers (preferably DANAKLON® ES C 1.7 dtex×6 mm bicomponent binder fibers comprising 50% sheath (polyethylene) and 50% core (polypropylene); (2) from about 75 to about 95% wood pulp fibers (preferably Southern Softwood Kraft fibers) and from about 5 to about 52% thermoplastic binder fibers (preferably PEXAFIL® polyethylene fibers), preferably KITTYHAWK® (a mixture of 80% Southern Softwood Kraft fibers and 20% PEXAFIL® polyethylene fibers in sheet form); (3) a mixture of from about 80 to about 90% (preferably about 85%) KITTYHAWK® and from about 10 to about 20% (preferably about 15%) hydrophilic nonbonding thermoplastic fibers (preferably high melting crimped polyester KODEL ® 431 fibers). These mixtures are preferably laid at a basis weight in the range of from about 60 to about 200 gsm, and most preferably in the range of from about 80 to about 180 gsm.

The wet caliper, wet density, and percent wet compression of some representative thermally bonded materials useful as primary distribution layers in the present invention are shown in Table 2 below:

TABLE 2

| Material | Wet Caliper (mils) | | Wet Density (g/cc) | | % Wet Compression | | Vertical Wicking (cm) | Basis Weight gsm |
|---|---|---|---|---|---|---|---|---|
| | at 0.041 psi | at 0.167 psi | at 0.041 psi | at 0.167 psi | at 0.041 psi | at 0.167 psi | | |
| 2* | 52.1 | 47.9 | 0.120 | 0.130 | 4.6 | 8.1 | 15 | 159 |
| 3** | 61.5 | 55.5 | 0.102 | 0.114 | 5.4 | 9.8 | 11.8 | 161 |
| 4*** | 89 | 76.9 | 0.078 | 0.091 | 7.9 | 13.6 | 10.5 | 178 |

*100% KITTYHAWK ® (80% Southern Softwood Kraft, 20% PLEXAFIL ®)
**85% Southern Softwood Kraft, 15% DANAKLON ® ES-C 1.7 dtex × 6 mm (65% sheath/35% core)
***85% KITTYHAWK ®, 15% KODEL ® 431 15 dtex × 0.5 mm In some cases, it can be desirable to provide integrated absorbent structures and/or cores. To provide such integrated structures and/or cores two or more air-laying heads are used to laydown the respective layers sequentially. Absorbent gelling material for the storage layer (with or without a carrier) can be added between the appropriate air-laying heads to provide integrated, laminate absorbent cores.

4. Fluid and Physical Properties of Absorbent Structures and Layers
   a. Vertical Wicking The capillary properties of the respective layers in the absorbent structures according to the present invention are particularly important in terms of the ability to acquire aqueous body fluids, especially menstrual fluids, and to move these acquired fluids to other remote regions of the absorbent structure. The capillarity of fibrous webs or matrices is often measured in terms of capillary suction. The secondary topsheets and secondary distribution layers have a relatively low capillary suction (and typically a relatively low density of from about 0.03 to about 0.07). As a result, these layers excel at acquiring and giving up menstrual fluids. By contrast, the primary fluid distribution layers according to the present invention have a relatively high capillarity (and typically a relatively high density of from about 0.075 to about 0.15). This means that the primary distribution layers are very good at moving acquired menstrual fluids not only in the Z-dimension, but also in the X-Y dimension.

It has been found that the ability to vertical wick artificial menstrual fluid (AMF) is a very good way to define the low/high capillary suction of these layers. Vertical wicking accounts for a variety of factors that affect capillary suction, including density (wet and dry), pore size, plastization of cellulosic fibers by the fluid, as well as the physical properties of the fluid being wicked (e.g., contact angle and surface tension). The secondary topsheets and secondary distribution layers have a relatively low vertical wicking values of from about 1 to about 6 cm of AMF, and typically from about 2 to about 4 cm of AMF. By contrast, the primary distribution layers according to the present invention have a relatively high vertical wicking value of from about 8 to about 20 cm of AMF, and typically from about 11 to about 16 cm. See Test Methods section for the procedure to measure vertical wicking values.

b. Wet Density of Primary Distribution Layer

The wet density of the primary fluid distribution layer, especially where there is no secondary distribution layer in the absorbent core has been found to have an important effect on the fluid uptake capacity and efficiency of the absorbent gelling material (AGM). As the level of AGM is increased in the storage layer, the AGM efficiency tends to drop. This is particularly shown in Table 3 below:

TABLE 3

| Primary Distribution Layer Material* | Wet Density at 0.041 psi (g/cc) | AGM B.W. (gsm) | Initial Uptake (g)** | Retained Uptake (g)** | AGM Efficiency (g/g)** |
|---|---|---|---|---|---|
| 2 | 0.120 | 56 | 36.9 | 25.7 | 18.6 |
|   |   | 112 | 18.2 | 17.7 | 3.4 |
|   |   | 185 | 28.5 | 25.6 | 5.6 |
|   |   | 0 | 27.2 | 12.2 |   |
| 3 | 0.102 | 56 | 37.3 | 25.4 | 19.4 |
|   |   | 112 | 37.8 | 28.8 | 12.2 |
|   |   | 185 | 37.5 | 30.5 | 8.2 |
|   |   | 0 | 35.3 | 13.0 |   |
| 4 | 0.078 | 56 | 38.2 | 23.9 | 16.0 |
|   |   | 112 | 48.0 | 32.4 | 14.3 |
|   |   | 185 | 45.9 | 33.2 | 9.0 |

*See Table 2 for composition; Material 1 (see Table 1) is used in secondary topsheet and "dusting" layer
**Measured by HGW While AGM efficiency can be improved by using a lower density primary distribution layers, this is not desirable since higher density distribution layers provide better topsheet dryness for catamenial pads. Accordingly, a balance is desirably struck between the wet density of the primary distribution layer and the amount of AGM in the storage layer for optimum AGM efficiency. For optimum efficiency in absorbent structures having no secondary distribution layer, the primary distribution layer preferably has a wet density in the range of from about 0.10 to about 0.15 g/cc and a storage layer comprising AGM in amount of from about 80 to about 150 gsm.

c. Inclusion of Secondary Distribution Layer

The inclusion of the secondary fluid distribution layer has also been found to have an important effect on the fluid uptake capacity and efficiency of the AGM. In absorbent structures where the absorbent core has only a primary fluid distribution layer, the density of the absorbent structure basically increases from the secondary topsheet to the primary fluid distribution layer, i.e., the absorbent structure has an increasing density gradient in the direction towards the storage layer. By contrast, absorbent cores having both primary and secondary fluid distribution layers in the absorbent core have in essence a dual density gradient in the direction towards the storage layer, i.e., an increase in density from the secondary topsheet to the primary distribution layer and a decreasing density from the primary distribution layer to the secondary distribution layer. The benefit of using an absorbent structure according to the present invention having a dual density gradient to improve AGM utilization as higher AGM levels and higher primary distribution layer densities is particularly shown in Table 4 below:

TABLE 4

| Primary Distribution Layer Material* | Wet Density at 0.041 psi (g/cc) | Density Gradient | AGM B.W. (gsm) | Initial Uptake (g)** | Retained Uptake (g)** | AGM Efficiency (g/g)** |
|---|---|---|---|---|---|---|
| 2 | 0.120 | dual | 112 | 39.5 | 32.0 | 13.4 |
|   |   | increasing | 112 | 18.2 | 17.7 | 3.4 |
| 3 | 0.102 | dual | 112 | 49.0 | 34.8 | 15.6 |
|   |   | increasing | 112 | 37.8 | 28.8 | 12.2 |
| 4 | 0.078 | dual | 112 | 56.5 | 32.2 | 13.6 |
|   |   | increasing | 112 | 48.0 | 32.4 | 14.3 |

*See Table 2 for composition; Material 1 (see Table 1) is used in secondary topsheet secondary distribution layer and "dusting" layer
**Measured by HGW With dual density gradient absorbent structures according to present invention, higher density distribution layers can be used to improve topsheet dryness, but without sacrificing reasonable AGM efficiency. The benefits of these dual density gradient absorbent structures is particularly evident when they are used in combination with an apertured formed film primary topsheet. This combination provides the greatest improvement in AGM efficiency for a higher density distribution layers that delivers better topsheet dryness. Indeed, the use of an apertured formed film topsheet improves the absorption performance of increasing density gradient absorbent structures to more closely approach that of the dual density absorbent structures. This is particularly shown in Table 5 below:

TABLE 5

| Distribution Layer Material* | Wet Density at 0.041 psi (g/cc) | Formed Film Top Sheet | Density Gradient | Initial Uptake (g)** | Retained Uptake (g)** | AGM Efficiency (g/g)** |
|---|---|---|---|---|---|---|
| 2 | 0.12 | without | dual | 39.5 | 32.0 | 13.4 |
|  |  | with | dual | 51.0 | 45.7 | 16.2 |
|  |  | without | increasing | 18.2 | 17.7 | 3.4 |
|  |  | with | increasing | 42.5 | 39.7 | 14.7 |
| 3 | 0.102 | without | dual | 49.0 | 34.8 | 15.6 |
|  |  | with | dual | 52.6 | 47.8 | 15.2 |
|  |  | without | increasing | 37.8 | 28.8 | 12.2 |
|  |  | with | increasing | 51.6 | 48.5 | 18.1 |
| 4 | 0.078 | without | dual | 56.5 | 32.2 | 13.6 |
|  |  | with | dual | 50.0 | 48.8 | 16.1 |
|  |  | without | increasing | 48.0 | 32.4 | 14.3 |
|  |  | with | increasing | 53.6 | 50.0 | 16.2 |

*See Table 2 for composition; Material 1 (see Table 1) is used in secondary topsheet, secondary distribution layer and "dusting" layer
**Measured by HGW d. Compressive Force and Recovery The absorbent structures according to the present invention have also been to impart physical properties to catamenial products that go beyond the ability to acquire, distribute and store fluids. When worn, catamenial pads and other related catamenial products are subjected to lateral compression forces. When these compressive forces are released, the pad then rebounds from its compressed state.

How the pad reacts to these compressive forces is important since it affects: (1) the comfort level associated with wearing the pad; (2) the amount of panty area covered by the pad (i.e., is relevant to the prevention of panty soiling experiences); and (3) the visual appearance of the pad after use. These compressive forces are often measured as the amount of force necessary to hold the central portion of the catamenial pad compressed in the cross (width) direction in both the dry and wet states. The resiliency of the pad is often measured as both the % recovery relative to the initial width of the pad and the absolute width recovered in the central portion of the pad after it has been subjected to cross directional compression.

The absolute width recovered after compression relates to the ability of the pad to sufficiently cover the panty to protect it from soiling. Additionally, catamenial users have referred to pads that have considerably narrower widths at the time of removal (relative to the pad before it is worn) as being poor for bunching. The % recovery of the pad after compression has been found to correlate to the visual appearance of the product after use.

Although compressive forces and recoveries are measured in both the dry and wet states, perceptions of comfort appear to be formulated as the pad is first being worn. This means that compressive forces and recoveries in the dry state are more relevant to comfort than are those in the wet state. It has been found that thin catamenial pads having compressive force values of about 300 g. or less, preferably about 200 g. or less, in the dry state are considered to be comfortable when worn. Typically, catamenial pads according to the present invention have preferably about 200 g. or less, in the dry state are considered to be comfortable when worn. Typically, catamenial pads according to the present invention have compressive force values in the dry state in the range of from about 50 to about 300 g., and more typically from about 100 to about 200 g.

Most catamenial products lose recovery as they become wet. This means the wet state of the pad is more critical to sustained area coverage of the panty than is the dry state. Pads which have an absolute compression value after wet compression of at least about 48 mm (preferably, at least about 55 mm) sufficiently cover the panty area to impact on the prevention of panty soiling. Typically, pads according to the present invention have a compression recovery value (at the center) after wet compression in the range of from about 48 to about 70 mm and more typically in the range of from about 55 to about 65 mm.

Similarly, since catamenial users make visual assessments of the pad after it has been worn for a period of time (i.e., when checking or removing the pad), the pad is more than likely to contain some amount of fluid. Thus, the wet state is important to the visual appearance of the product after use. Pads which recover (at the center) from the wet compressed state at least about 65% (preferably at least about 75%) of their initial width appeal to catamenial users for their visual appearance after use. Pads according to the present invention typically recover after wet compression from about 55 to about 90% (more typically from about 75 to about 85%) of the initial pad width.

See Test Methods section for the procedure to measure the compressive force values in the dry state, and the absolute and relative recovery from compression (i.e., resiliency) in the wet state of catamenial pads and related catamenial products.

D. Catamenial Pads Sanitary. Napkins and Related Absorbent Articles

A preferred embodiment of a catamenial pad or sanitary napkin 10 according to the present invention is shown in FIG. 1. As used herein, the term "sanitary napkin" refers to an absorbent article that is worn by females adjacent to the pudendal region, generally external to the urogenital region, and which is intended to absorb and contain menstrual fluids and other vaginal discharges from the wearer's body (e.g., blood, menses, and urine). Interlabial devices that reside partially within and partially external of the wearer's vestibule are also within the scope of this invention. As used herein, the term "pudendal" refers to the externally visible female genetalia. It should be understood, however, that the present invention is also applicable to other feminine hygeine of catamenial pads, such as panty liners or other absorbent articles such as incontinence pads, or the like.

Figure 2:
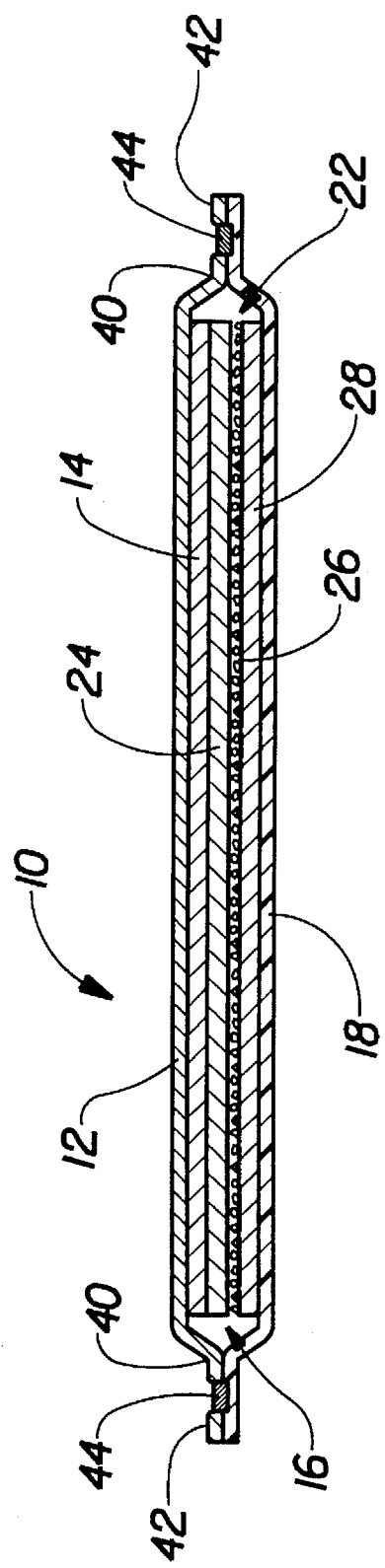
FIG. 2 is a cross-sectional view take along line 2—2 of FIG. 1.

As best seen from FIG. 2, catamenial pad 10 is constructed of fluid pervious primary topsheet 12, a fluid acquiring secondary topsheet 14, an absorbent structure indicated generally as 16, and fluid impervious backsheet 18. The backsheet 18 and the topsheet 12 are positioned adjacent the garment surface and the body surface, respectively, of pad 10 and are preferably joined to each other. For example, the backsheet 18 and the topsheet 12 can be secured to each other by adhesive. Adhesives that have been found to be satisfactory are manufactured by H. B. Fuller Company of St. Paul, Minn. under the designation HL-1258 or H-2031. Alternatively, topsheet 12 and backsheet can be joined to each other by heat bonding, pressure bonding, ultrasonic bonding, dynamic mechanical bonding, or any other suitable method for joining topsheets and backsheets known in the art.

A particularly suitable method for joining topsheet 12 and backsheet 18 together is by a crimp seal. As shown in FIG. 1, the lateral edges of absorbent structure 16 define a perimeter 40. The primary topsheet 12 and backsheet 18 each have a shape similar to, but larger than, absorbent structure 16. Thus, topsheet 12 and backsheet 18 each have a portion that extends outwardly from perimeter 40 of the absorbent structure 16 to define a continuous border segment that encircles the absorbent structure. Border segment 42 is generally relatively narrow, and can extend a distance of approximately 0.25 to 6 mm. and preferably is approximately 3 mm. wide. However, the width of border 42 can be uniform or vary about the perimeter of pad 10. Moreover, border segment 42 is relatively thin and flexible and is intended to provide improved protection against soiling of the vicinity surrounding the discharge region.

A fluid impermeable seal 44 is provided in border segment 42 that surrounds perimeter 40. Thus, seal 44 is adapted to prevent lateral migration (i.e., "wicking") of fluid from perimeter 40 of absorbent structure 16 through border segment 42 toward the peripheral edges of catamenial pad 10, thereby inhibiting premature side soiling of the wearer's undergarments. As a result, topsheet 12 and backsheet 18, tend to remain relatively free of fluids. Seal 44 is preferably disposed laterally inwardly as close as possible to perimeter 40 so that a greater portion of border segment 42 remains dry and unsoiled. Seal 44 preferably completely surrounds perimeter 40 without any gaps that would allow wicking and fluid leakage.

Seal 44 is preferably formed by the simultaneous application of pressure, with or without heat, commonly referred to as a "crimping" operation. During the "crimping" process, sufficient pressure, optionally with heat, is applied to melt topsheet 12 and backsheet 18, thereby forming seal 44. Portions of border 42 outside of seal 44 are crimped with discrete spaced-apart bonds. This discrete bonding creates a reverse or negative capillary gradient so that any fluids inadvertently passing through seal 44 will tend to be attracted toward the more dense material in the area of seal 44; any fluid movement outside seal 44 occurs along seal 44, as opposed to toward outer edge of border 42.

One embodiment of an absorbent structure 16 according to the present invention used in catamenial pad 10 is shown in FIG. 2. As shown in FIG. 2, this particular absorbent structure 16 comprises a secondary topsheet 14 and an absorbent core 22 in fluid communication with the secondary topsheet. If desired, the secondary topsheet can be joined to the absorbent core by a suitable adhesive, or by other types of bonding such as thermal bonding.

Absorbent core 22 is shown in FIG. 2 as comprising three components: a fluid distribution layer 24, a fluid storage layer 26 and fibrous "dusting" layer 28. In forming this absorbent core, the "dusting" layer 28 provides the initial layer upon which the absorbent gelling material of the storage layer 26 is deposited. The distribution layer 24 is then positioned over the deposited absorbent gelling material thus forming a laminate-type structure. Although it is possible to join dusting layer 28 and distribution layer 26 through the use of an adhesive, these two layers are typically joined together by thermal bonding since each of these layers comprise some thermoplastic material, typically thermoplastic binder fibers.

Figure 3:
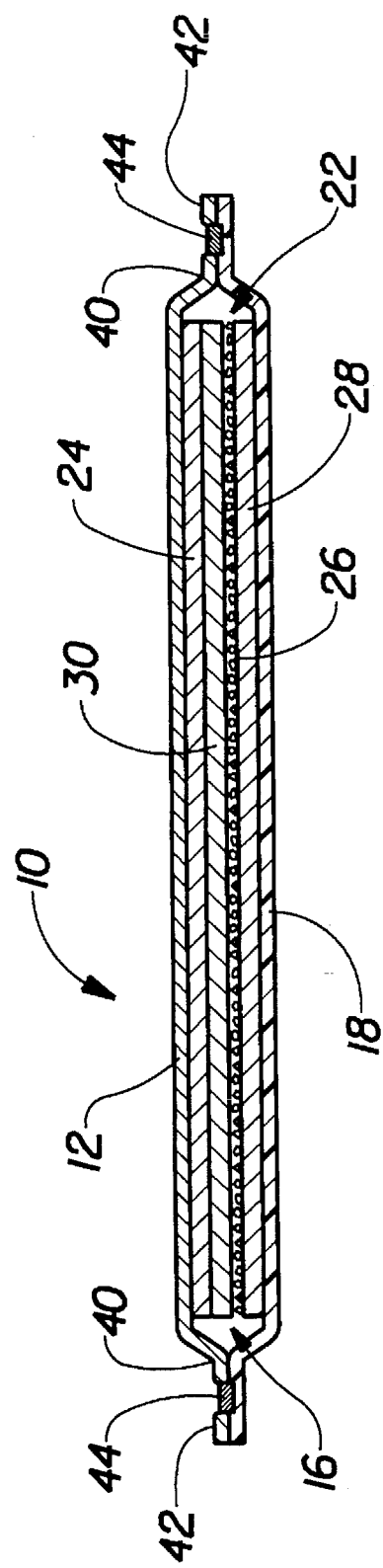
FIG. 3 is a cross-sectional view showing an alternative absorbent structure according to the present invention.

Another embodiment of absorbent structure 16 is shown in FIG. 3. As shown in FIG. 3, absorbent structure 16 comprises an absorbent core 22, but no secondary topsheet. In this embodiment, absorbent core 22 comprises four components: a primary fluid distribution layer 24, a secondary fluid distribution layer 30, a fluid storage layer 26 and fibrous "dusting" layer 28. (In the case pantiliners and other light incontinence pads, storage layer 26 and "dusting" layer 28 can be optional, but preferred components.) Again, the "dusting" layer 28 provides the point for depositing the absorbent gelling materials of storage layer 26. The secondary and primary distribution layers 30 and 24 are then positioned over the deposited absorbent gelling material to form a laminate-type structure. This laminate is typically joined together by thermal bonding.

Figure 4:
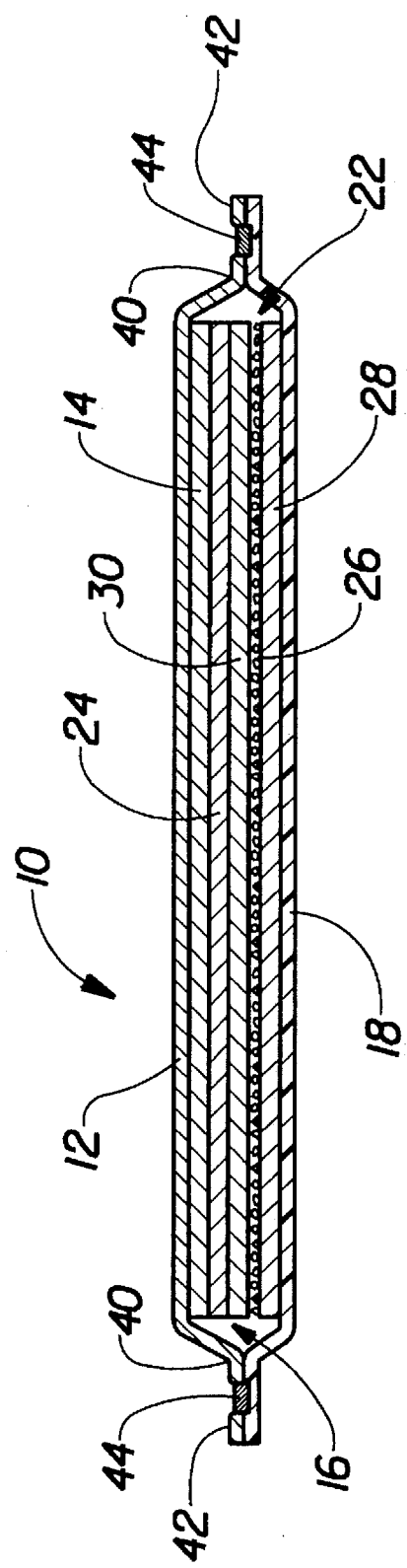
FIG. 4 is a cross-sectional view showing another alternative absorbent structure according to the present invention.

FIG. 4 shows a combination of the embodiments shown in FIGS. 2 and 3. Like the embodiment shown in FIG. 2, absorbent structure 16 of FIG. 4 comprises a secondary topsheet 14 and an absorbent core 22. Like the embodiment shown in FIG. 3, absorbent core 22 of FIG. 4 comprises four components: a primary fluid distribution layer 24, a secondary fluid distribution layer 30, a fluid storage layer 26 and fibrous "dusting" layer 28. The absorbent structure 16 of FIG. 4 provides a combination of the desired fluid handling features of the embodiment of FIG. 2 with the embodiment of FIG. 3.

The backsheet 18 is impervious to liquids (e.g., menses and/or urine) and is preferably manufactured from a thin plastic film, although other flexible liquid impervious materials may also be used. As used herein, the term "flexible" refers to materials that are compliant and will readily conform to the general shape and contours of the human body. The backsheet 18 prevents the exudates absorbed and contained in the absorbent core 22 from wetting articles that contact the sanitary napkin 10 such as pants, pajamas and undergarments. The backsheet 18 can comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance. Further, the backsheet 18 can permit vapors to escape from the absorbent structure 16 (i.e., breathable) while still preventing exudates from passing through the backsheet 18.

The topsheet 12 is compliant, soft feeling, and non-irritating to the wearer's skin. Further, the topsheet 12 is fluid pervious permitting fluids (e.g., menses and/or urine) to readily penetrate through its thickness. A suitable topsheet 12 can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

Preferred topsheets for use in the present are selected from high loft nonwoven topsheets and aperture formed film topsheets. Apertured formed films are especially preferred for the topsheet because they are pervious to body exudates and yet non-absorbent and have a reduced tendency to allow fluids to pass back through and rewet the wearer's skin. Thus, the surface of the formed film that is in contact with the body remains dry, thereby reducing body soiling and creating a more comfortable feel for the wearer. Suitable formed films are described in U.S. Pat. No. 3,929,135 (Thompson), issued Dec. 30, 1975; U.S. Pat. No. 4,324,246 (Mullane, et al.), issued Apr. 13, 1982; U.S. Pat. No. 4,342,314 (Radel. et al.), issued Aug. 3, 1982; U.S. Pat. No. 4,463,045 (Ahr et al.), issued Jul. 31, 1984; and U.S. Pat. No. 5,006,394 (Baird), issued Apr. 9, 1991. Each of these patents are incorporated herein by reference. Particularly preferred microapetured formed film topsheets are disclosed in U.S. Pat. No. 4,609,518 (Curro et al), issue Sep. 2, 1986 and U.S. Pat. No. 4,629,643 (Curro et al), issued Dec. 16, 1986, which are incorporated by reference. The preferred topsheet for the present invention is the formed film described in one or more of the above patents and marketed on sanitary napkins by The Procter & Gamble Company of Cincinnati, Ohio as "DRI-WEAVE."

The body surface of the formed film topsheet can be hydrophilic so as to help liquid to transfer through the topsheet faster than if the body surface was not hydrophilic so as to diminish the likelihood that menstrual fluid will flow off the topsheet rather than flowing into and being absorbed by the absorbent structure. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated by reference. Alternatively, the body surface of the topsheet can be made hydrophilic by treating it with a surfactant such as is described in the above referenced U.S. Pat. No. 4,950,254, incorporated herein by reference.

In use, pad 10 can be held in place by any support or attachment device (not shown) well-known for such purposes. Preferably, pad 10 is placed in the user's undergarment or panty and secured thereto by a fastener such as an adhesive. The adhesive provides a means for securing the pad in the crotch portion of the panty. Thus, a portion or all of the outer surface of the backsheet 18 is coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before pad 10 is placed in use, the pressure-sensitive adhesive is typically covered with a removable release liner in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/0 both of which are manufactured by the Akrosil Corporation of Menasha, Wis. The pad 10 is put in use by removing the release liner and thereafter placing the pad in a panty so that the adhesive contacts the panty. The adhesive maintains the pad 10 in its position within the panty during use.

E. Test Methods

1. Vertical Wicking a. Preparation of Artificial Menstrual Fluid

Step 1: Dilute 2.5 ml of reagent grade 85–95% lactic acid to 27.5 ml with distilled water. Label as 8% lactic acid.

Step 2: Mix 10.0 gm of KOH with 90 ml distilled water until completely dissolved. Label as 10% potassium hydroxide solution.

Step 3: Add 8.5 gm sodium chloride and 1.38 gm hydrous monobasic sodium phosphate to a flask and dilute to 1000 ml with distilled water. Mix until completely dissolved. Label as monobasic sodium phosphate solution.

Step 4: Add 8.5 gm sodium chloride and 1.42 gm anhydrous dibasic sodium phosphate to a flask and dilute to 1000 ml with distilled water. Mix until completely dissolved. Label as dibasic sodium phosphate solution.

Step 5: Add 450 ml of the dibasic sodium phosphate solution to a 1000 ml beaker and add monobasic sodium phosphate solution until the pH is lowered to 7.2±0.1. Label as phosphate solution.

Step 6: Mix 460 ml of phosphate solution and 7.5 ml of 10% potassium hydroxide solution in a 1000 ml beaker. Heat solution to 50° C. and then add 31 gm sterilized gastric mucin (ICN Biomedical Inc., Cleveland, Ohio). Continue heating for 2.5 hours to completely dissolve the gastric mucin. Allow the solution to cool to less than 40° C. and then add 2.0 ml of 8% lactic acid solution. Autoclave mixture at 121° C. for 15 minutes, then allow to cool to room temperature. Mucous mixture should be used within 7 days. Label as gastric mucin solution.

Step 7: Mix 500 ml of gastric mucin solution and 500 ml of fresh, sterile defibrinated sheep blood (Cleveland Scientific, American Biomedical, Bath, Ohio) in a beaker. Label as artificial menstrual fluid. Store refrigerated and use within 7 days.

b. Test Procedure (1) Sample Preparation

Samples to be tested should be equilibrated for a minimum of two hours in a room conditioned to 73°±2° F. and 50±2% relative humidity. Samples should be cut into 1 inch strips that are at least 25 cm in height. Three samples should be cut for each material that is to be tested.

After the samples have equilibrated, the samples should be sealed in plastic on the top and on both long sides using a T-Bar sealer (Model T-7, 115VAC, 65 W Harwil Company, Santa Monica, Calif.). One half of a centimeter of the bottom of the material strip should remain exposed. The outside of the plastic is marked at each centimeter along the length of the sample, starting at the bottom of the plastic (not the bottom of the sample).

(2) Equipment Preparation

While slowly stirring with magnetic stir bar, the artificial menstrual fluid is allowed to equilibrate for 30 minutes to room temperature. Approximately 500 ml of the equilibrated artificial menstrual fluid is poured into a flat bottomed glass dish (or enough to allow the level of fluid in the dish to be approximately 1.5 inches deep). The filled dish, with magnetic stir bar, is placed on a magnetic stir plate set at low speed.

A cylindrical Plexiglas bar (12 inch cylindrical bar with at least two attached Plexiglas plates (25 cm×0.5 cm×3 cm) attached at the end with the spacing being adjustable) is clamped onto a ring stand. The clamp should tentatively be set approximately 18–20 inches above the base of the stand.

Allow Enough space between the Plexiglas plates on the end of the cylindrical bar is provided to fit the thickness of the samples to be tested.

(3) Carrying Out Test Procedure

The sealed top side of the sample is placed between two of the Plexiglas plates, and then the plates are tightened together until the sample is completely suspended. There should be enough room along the width of the plates to fit 2–3 samples without the samples touching. If not, additional plates can be used to position the samples one behind the other. After suspending all samples, the bottom and top of the samples should all be level with respect to the Plexiglas plates and each other.

The stir plate and dish of artificial menstrual fluid is placed directly underneath the suspended samples. The samples are lowered such that 0.5 cm of each sample is submerged in the artificial menstrual fluid. (The plastic covered portion of the samples should not be submerged, as fluid will tend to wick in the interfaces of the seal instead of within the sample). Adjustments to level the bar and samples are made, if necessary, so that each sample bottom is equally submerged in the artificial menstrual fluid.

Fluid will rise within the sample very quickly at first, and then slower over time. In addition, the height of the fluid is usually higher on the edges of the sample (where the sample has been compressed during cutting) and lower in the center of the sample. The fluid height should always be read from the bottom of the meniscus.

The height of the fluid should be recorded every half hour from the time the sample is first submerged. Samples should be wicked a minimum of 5 hours. However, if no change is seen in the wicking height after one hour, this height is recorded as the final vertical wicking height. The average of the final vertical wicking values recorded for the samples (n=3) is used as the vertical wicking value for the material.

2. Horizontal Gravimetric Wicking Test

Horizontal Gravimetric Wicking (HGW) is an absorbence test that measures the uptake of fluid by a 2.5 in. by 7.5 in. absorbent core or catamenial product sample as a function of time. In this method, the sample is held upside down horizontally in a holder suspended from an electronic balance. A glass supply tube, containing the test fluid (in this case, artificial menstrual fluid) and connected to a fluid reservoir at zero hydrostatic head relative to the test sample, is allowed to contact the lower surface of the sample as a point source and the increase in weight of the sample is used as a measure of fluid uptake versus time. The test proceeds for 3900 seconds. During the test, the sample is constrained under 0.18 psi pressure by a conformable water-filled plastic bag covered by a metal weight. This conformable system provides a hydrostatic pressure to the sample to allow the pressure on the sample to remain relatively constant over the entire sample area.

"Initial Uptake" is defined as the weight of artificial menstrual fluid absorbed by the system after 3900 seconds. "Rewet" is subsequently measured on the absorbent structure or catamenial pad to find out the amount of fluid that can be repeatedly blotted from the structure/pad with Whatman filter paper at 0.25 psi until the core will give up less than 0.5 grams of AMF. "Retained Uptake" is calculated as the difference between "Initial Uptake" and "Rewet".

"Absorbent Gelling Material (AGM)" Efficiency" (gm/gm) is measured for storage layers comprising 100% AGM by removing all of the layers except the storage and "dusting" layers after the HGW test and weighing the storage and dusting layers. The "AGM Efficiency" is calculated as the combined weight of the wetted storage and "dusting" layers, minus the dry weight of "dusting" layer and dry AGM, and then divided by the dry weight of AGM.

3. Compressive Force and Recovery Test

In this test, the center of a catamenial pad is subjected to 6 cycles of compression across its width, followed by release of the compressive forces. (This test can also be used with other catamenial products such pantiliners). The pad is compressed by a pair of plates designed to simulate forces and constraints experienced during wear. The distance traveled by the plates and the resulting forces are measured.

4. Apparatus and Sample Preparation

Figure 5:
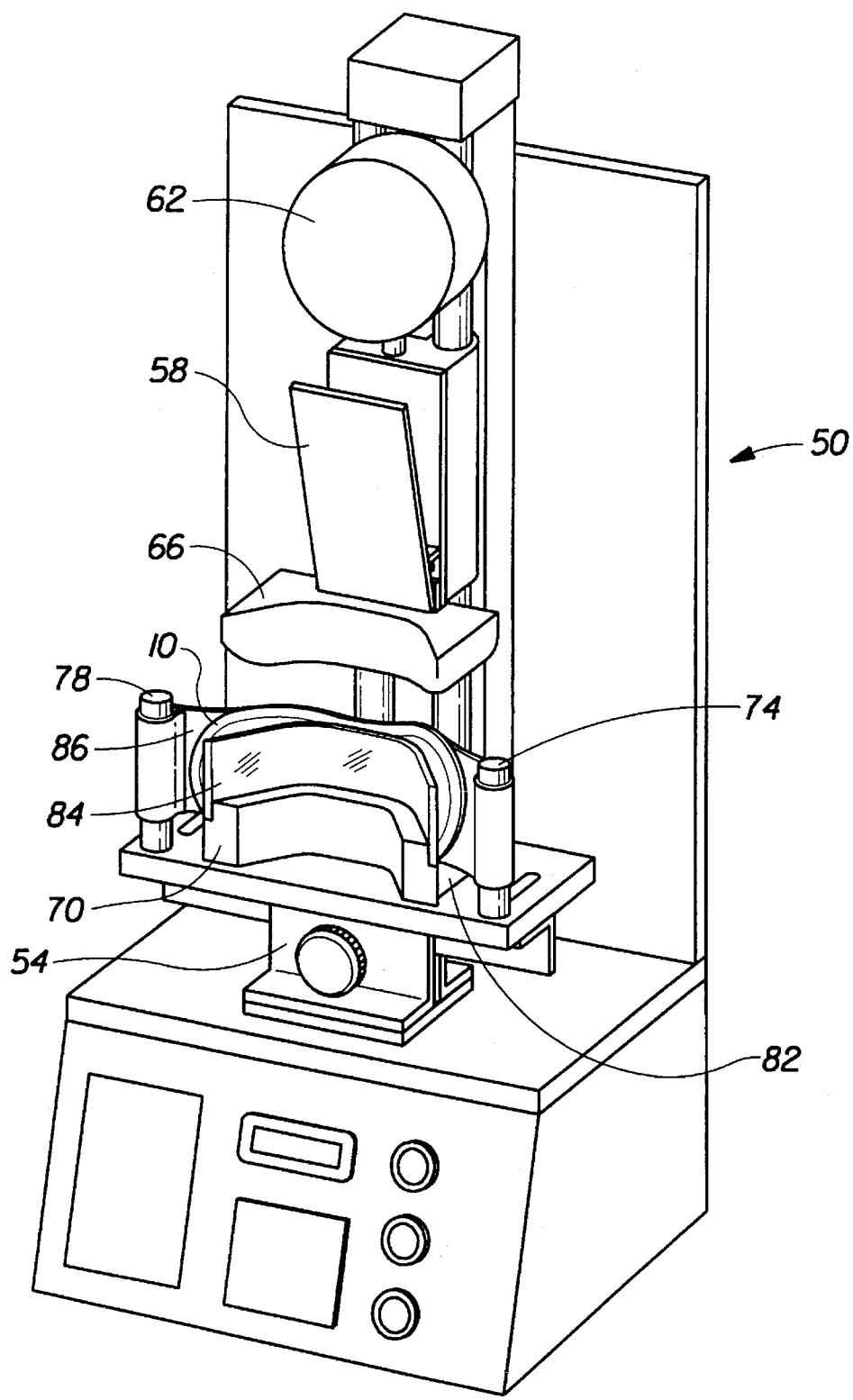
FIG. 5 is a perspective view of an instrument for measuring the compressive force and resiliency of a catamenial pad.

Suitable equipment for carrying out this test include, for example, Instron Model 1122 and EME Model 599A instruments. FIG. 5 shows this test being performed with an EME 599A instrument indicated generally as 50. Instrument 50 includes an fixed lower clamp 54 and an upper reciprocating clamp 58. Instrument 50 also includes a weight (4000 g) indicated generally as 62 for biasing upper clamp 58 downwardly.

Compressive forces are applied to the pad 10 by an assembly 64 (see FIGS. 6 and 7) comprised of a pair of plates 66 and 70. The upper compression plate 66 simulates one thigh of the wearer. The lower compression plate 70 simulates both the opposite thigh of the wearer and the portion of the body (the perineal area) contacting the pad 10 during use. The lower compression plate 70 also contains two spaced cylindrical posts 74 and 78, one on each side of main body portion 82 of lower plate 70, as well as a Plexiglas viewing screen 84 mounted on top of body portion 82. These posts 74 and 78 hold the crotch part of a panty 86 for attachment of pad 10. (The crotch portion of a suitable panty is cut out from a panty and provided with a sewn tube at either end for attachment to the posts 74 and 78).

Figure 6:
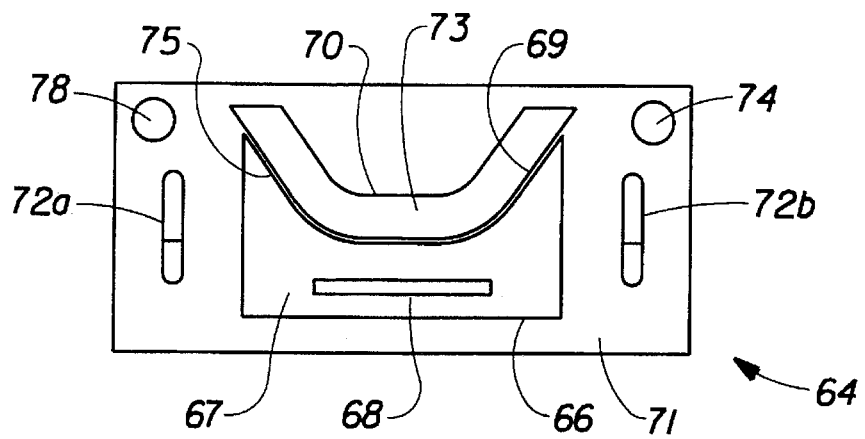
FIG. 6 is a top plan view of the compression plate assembly used in measuring the compressive force and resiliency of the catamenial pad.
Figure 7:
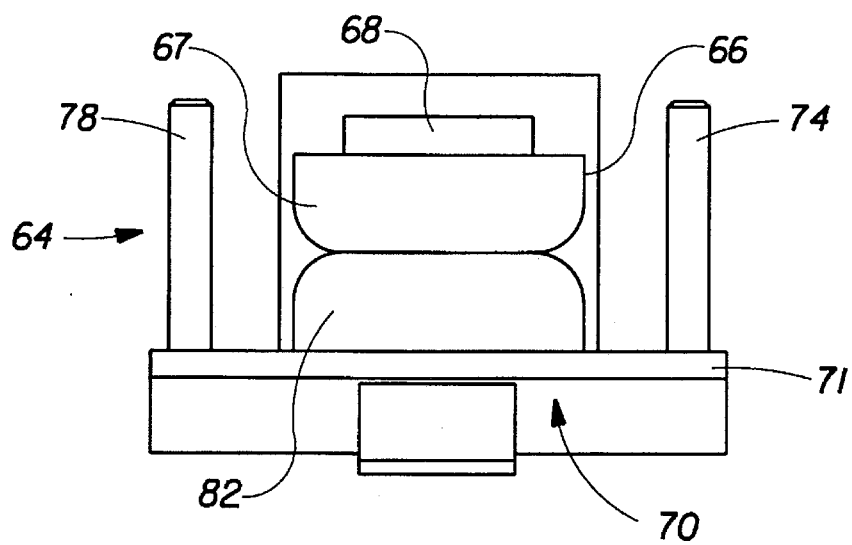
FIG. 7 is a side view of the compression plate assembly shown in FIG. 6.

Referring to FIGS. 6 and 7, lower plate 70 comprises a base 71 in which are formed a pair of spaced lots 72a and 72b that are used to secure plate 70 to lower clamp 54 of instrument 50. As particularly shown in FIG. 6, main body portion 82 of plate 70 has an upper part 73 provided with a convex, curved face 75.

Figure 8:
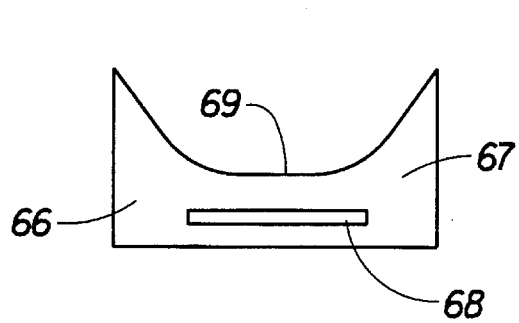
FIG. 8 is a top plan view of the of the upper compression plate of the compression plate assembly shown in FIGS. 6–7.
Figure 9:
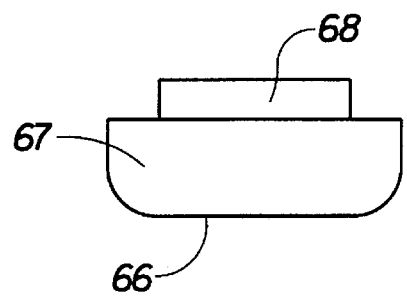
FIG. 9 is a side view of the upper compression plate assembly shown in FIG. 8.

As particularly shown in FIGS. 8 and 9, upper plate 66 has a main body portion 66 that is provided with a concave, curved face 69. Attached to body portion 67 is a generally rectangular mounting bracket 68 for securing the upper plate 66 to the reciprocating upper clamp 58 of instrument 50. As particularly shown in FIG. 6, convex face 75 of lower plate 70 is opposed and configured so as to fit within concave face 69 of upper plate 66. This configuration allows upper plate 66 to move past lower plate 70 in close proximity thereto, but without faces 75 and 69 coming into contact. As shown particularly in FIG. 6, when upper plate 66 moves completely down, it fits together with lower plate 70 but without coming into physical contact.

The plates 66 and 70 (and their constituent parts) can be made from any suitable material (e.g., aluminum, Lexan, Plexiglas) that can be formed into the required shape. However, the weight of assembly 64 comprising plates 66 and 70 must be significantly lower than the limit of the instrument load cell to allow sufficient range for the force measurement.

During the test, the crosshead speed (i.e., the rate at which upper plate 66 moves downward during the compression cycle) is 22 inches/minute. The gap between the upper part 73 of main body portion 82 of plate 70 and the bottom of main body portion 67 of plate 66 starts at a distance of 4 inches, and then narrows to a 1 inch gap distance when pad 10 is fully compressed.

Samples of catamenial pad 10 are equilibrated for a minimum of two hours at 73°±2° F., and 50±2% relative humidity. Samples should be fully finished pads, including placement of adhesive and release paper on the bottom of the pad. Undue bending of the sample as it is being prepared should be avoided. A minimum of six samples of each pad 10 is required for the test.

b. Test Procedure

The release paper is removed from the pad 10 and then the pad is centered on the panty crotch portion 86 with respect to the seams. Pad 10 is then pressed down lightly to insure it is secured. The sewn tubes on the ends of panty crotch portion 86 are then slid onto the poles of lower compression plate 70. Pad 10 should be in the configuration of an arc with its ends pointing toward the main body portion 82 of plate 70, and should be loosely confined between the panty crotch portion 86 and the lower part of body portion 82. Pad 10 is oriented such that it is standing up on one edge. The distance between the upper part 73 of main body portion 82 of plate 70 and the bottom of main body portion 67 of plate 66 should now be 4 inches.

The plate 66 is then moved towards plate 70 at a rate of 22 inches/minute by the downward motion of reciprocating upper clamp 58 until pad 10 has been compressed to 1 inch (full compression). Compression is maintained for 30 seconds. The distance at which the main body portion 67 of upper compression plate 66 makes contact with the edge of pad 10 is determined when a force of 10 g is reached. This is the initial width of the pad. The force at the end of the 30 seconds after full compression is reached, and immediately before the compression is released, is recorded as the compression force.

After 30 seconds of full compression, the compressive forces are released by moving plate 66 to its initial position (4 inches apart). Pad 10 is left uncompressed for 60 seconds. At the end of the 60 seconds, a second compression cycle is started. The same procedure as described before is carried out. This procedure is repeated until pad 10 has been subjected to 6 compression/release cycles.

Three dry samples of pad 10 are tested by this procedure. Three additional samples of pad 10 are then tested in the wet state by pouring 7.5 ml of 0.9% saline solution into the center of the samples (allowing the sample to distribute the fluid itself), followed by 10 minutes before testing begins. The wet samples are subjected to the same procedure as the dry samples.

c. Calculations

After 3 dry samples and wet samples are run, the following values are determined:

(1) The average compression force from cycle 6 on the three dry pads;

(2) The average initial pad width from cycle 6 on the three wet pads;

(3) The average percent width on the three wet pads is calculated using the following equation:

% pad width=100×(initial pad width cycle 6÷initial pad width cycle 1)

F. Preparation of Catamenial Pads Having Improved Resistance to Bunching

Catamenial pads are constructed as follows. All materials are precut into the desired shapes (see FIG. 1). The absorbent structure layers are cut into rectangles measuring 65 mm by 207 mm. The topsheet and backsheet are also cut into rectangles measuring 127 mm by 292 mm.

Onto silicone-coated release paper a spiral pattern of of H2031 Findlay hot melt adhesive is applied at 0.02 g per in$^2$. This adhesive layer is transferred onto the bottom side of an aperture form film topsheet by rolling the topsheet and coated release paper together with a hand roller. The secondary topsheet is applied to the adhesive side of the topsheet and the two are bonded by rolling them together with a hand roller. Two strips of double sided-tape are applied on along both long sides of a polyethylene backsheet. The fibrous "dusting" layer is laid onto the double sided-tape and bonded by lightly rolling them together. The other layers of the absorbent core are added one at a time to construct the complete absorbent structure.

The topsheet and absorbent structure assembly are then combined. The edges of the product are sealed with an appropriately shaped die, attached to an iron and heated to a temperature above the melting point of the polyethylene topsheet and backsheet. The iron die is applied to the material with hand pressure to seal the edges. The catamenial pad is then cut from the excess material using a pair of hand scissors.

The materials used in constructing these pads and the mechanical properties of the resulting pads are shown in Tables 6 and 7 below:

TABLE 6

| Pad | A | B | C |
| --- | --- | --- | --- |
| Topsheet Material | Microapertured film | DRI-WEAVE | DRI-WEAVE. |
| Secondary Topsheet Material | Same as Material 1 in Table 1, 42 gsm | Same as Material 1 in Table 1, 42 gsm | Same as Material 1 in Table 1, 40 gsm |
| Primary Distribution Layer | KITTY-HAWK ®, 100 gsm | KITTY-HAWK ®, 200 gsm | KITTY-HAWK ®, 100 gsm |
| Storage Layer | Nalco AGM, 50 gsm | Nalco AGM, 50 gsm | Nalco AGM, 50 gsm |
| "Dusting" Layer | 90% Flint River Pulp/ 10% Danaklon ES-C fibers (3.3 dtex × 6 mm), 20 gsm | (1) 90% Flint River Pulp/10% Danaklon ES-C fibers (3.3 dtex × 6 mm), 40 gsm; and (2) 70% Flint River Pulp 15% Eastman Kodel 431 polyester fibers 15% Danaklon ES-C fibers (3.3 dtex × 6 mm), 50 gsm | 90% Flint River Pulp/ 10% Danaklon ES-C fibers (3.3 dtex × 6 mm), 40 gsm |

TABLE 7

| Pad | A | B | C |
| --- | --- | --- | --- |
| Compression Force dry | 70 g | 176 g | 94 g |
| Compression Recovery wet | 48 mm; 67% | 50 mm; 66% | 50 mm; 68% |

What is claimed is:

1. A catamenial pad capable of acquiring, distributing and storing aqueous body fluids, which comprises:

(A) a fluid pervious topsheet selected from the group consisting of apertured formed film topsheets and high loft nonwoven topsheets;

(B) an absorbent core in fluid communication with said topsheet and having:

(1) a primary fluid distribution layer comprising a mixture of hydrophilic cellulosic fibers and thermoplastic material bonding said fibers together into a thermally bonded matrix;

(2) a fluid storage layer in fluid communication with said primary layer, and comprising from about 15 to 100% by weight of said storage layer of absorbent gelling material and from 0 to about 85% by weight of said storage layer of a carrier for said absorbent gelling material;

(D) a fluid impervious backsheet;

(E) wherein the pad has:

(1) a compressive force value in the dry state of about 300 g or less;

(2) an absolute recovery from compression value in the wet state of at least about 48 mm; and (3) a relative recovery from compression value in the wet state of at least about 65% of the initial pad width.

2. An absorbent core for aqueous body fluids, which comprises:

(A) a primary fluid distribution layer comprising a mixture of hydrophilic cellulosic fibers and thermoplastic material bonding said fibers together into a thermally bonded matrix providing vertical wicking of from about 8 to about 20 cm of artificial menstrual fluid;

(B) a secondary fluid distribution layer in fluid communication with, and which can partition aqueous body fluids from, said distribution layer, said secondary distribution layer comprising a mixture of hydrophilic cellulosic fibers and thermoplastic material bonding said fibers together into a thermally bonded matrix providing vertical wicking of from about 1 to about 6 cm of artificial menstrual fluid;

(C) a fluid storage layer in fluid communication with said secondary distribution layer and comprising from about 15 to 100% by weight of said storage layer of absorbent gelling material and from 0 to about 85% by weight of said storage layer of a carrier for said absorbent gelling material.

3. A catamenial product which comprises a fluid pervious topsheet made from an apertured formed film or nonwoven material; a fluid impervious backsheet; and the absorbent core of claim 2 positioned between said topsheet and said backsheet.

4. The catamenial product of claim 3 which is selected from the group consisting of pantiliners and incontinence pads.

5. The absorbent structure of claim 2 which further comprises a fibrous layer (D) adjacent said storage layer and comprising a mixture of hydrophilic cellulosic fibers and thermoplastic material bonding said fibers together into a thermally bonded matrix.

6. The absorbent core of claim 5 in which at least two layers (A), (B), and (D) are integrated together by thermal bonding.

7. An absorbent structure for aqueous body fluids, which comprises:

(A). a fluid acquisition layer comprising a mixture of hydrophilic cellulosic fibers and thermoplastic material bonding said fibers together into a thermally bonded matrix providing vertical wicking of from about 1 to about 6 cm of artificial menstrual fluid;

(B) a fluid distribution layer in fluid communication with, and which can acquire aqueous body fluids from, said acquisition layer, said distribution layer comprising a mixture of hydrophilic cellulosic fibers and thermoplastic material bonding said fibers together into a thermally bonded matrix providing vertical wicking of from about 8 to about 20 cm of artificial menstrual fluid;

(C) a fluid storage layer in fluid communication with said distribution layer and comprising from about 15 to 100% by weight of said storage layer of absorbent gelling material and from 0 to about 85% by weight of said storage layer of a carrier for said absorbent gelling material.

8. A catamenial product which comprises a fluid pervious topsheet made from an apertured formed film or nonwoven material; a fluid impervious backsheet and the absorbent structure of claim 7 between said topsheet and said backsheet.

9. The product of claim 8 selected from the group consisting of pantiliners and incontinence pads.

10. The absorbent structure of claim 7 wherein said thermally bonded matrices of said acquisition layer (A) provides vertical wicking of from about 2 to about 4 cm of artificial menstrual fluid.

11. The absorbent structure of claim 10 wherein said acquisition layer (A) has a wet density in the range of from about 0.03 to about 0.07 g/cc.

12. The absorbent structure of claim 10 wherein said thermally bonded matrix of said distribution layer (B) provides vertical wicking of from about 11 to about 16 cm of artificial menstrual fluid.

13. The absorbent structure of claim 12 wherein said distribution layer (B) has a wet density in the range of from about 0.075 to about 0.15 g/cc.

14. The absorbent structure of claim 13 wherein said distribution layer (B) has a wet density in the range of from about 0.10 to about 0.15 g/cc and wherein said storage layer (C) comprises absorbent gelling material in an amount of from about 80 to about 150 gsm.

15. The absorbent structure of claim 7 which further comprises a fibrous layer (D) adjacent said storage layer and comprising a mixture of hydrophilic cellulosic fibers and thermoplastic material bonding said fibers together into a thermally bonded matrix.

16. The absorbent structure of claim 15 in which at least two of layers (A), (B), and (D) are integrated together by thermal bonding.

17. The absorbent structure of claim 15 wherein said thermally bonded matrices of each of said layers (A), (B) and (D) are formed from a mixture of comprising from about 10 to 95% wood pulp fibers and from about 5 to about 90% thermoplastic binder fibers.

18. The absorbent structure of claim 17 wherein storage layer (C) comprises from about 30 to 100% absorbent gelling materials and from 0 to about 70% carrier.

19. The absorbent structure of claim 18 wherein storage layer (C) comprises from about 60 to 100% absorbent gelling materials and from 0 to about 40%, carrier.

20. The absorbent structure of claim 17 wherein said thermally bonded matrices of each of said layers (A), (B) and (D) are formed from a mixture comprising from about 55 to about 90% wood pulp fibers and from about 10 to about 45% thermoplastic binder fibers.

21. The absorbent structure of claim 20 wherein thermally bonded matrix of said layer (B) is formed from a mixture having a basis weight of from about 50 to about 200 gsm and comprising from about 80 to about 90% wood pulp fibers and from about 10 to about 20% thermoplastic bicomponent binder fibers.

22. The absorbent structure of claim 20 wherein said thermally bonded matrix of said layer (B) is formed from a mixture having a basis weight of from about 80 to about 180 gsm and comprising from about 85 to about 95% wood pulp fibers and from about 5 to about 15% thermoplastic binder fibers.

23. The absorbent structure of claim 20 wherein said thermally bonded matrix of said layer (A) is formed from a mixture having a basis weight of from about 40 to about 60 gsm. and comprising from about 45 to about 90% wood pulp fibers; up to about 30% hydrophilic nonbonding thermoplastic fibers, and from about 5 to about 50% thermoplastic bicomponent binder fibers.

24. The absorbent structure of claim 23 wherein said thermally bonded matrix of said layer (A) is formed from a mixture having a basis weight of from about 45 to about 55 gsm and comprising from about 65 to about 90% wood pulp fibers, from about 10 to about 20% hydrophilic nonbonding thermoplastic fibers, and from about 10 to about 20% thermoplastic binder fibers.

25. The absorbent structure of claim 23 wherein said thermally bonded matrix of said layer (D) is formed from a mixture comprising from about 85 to about 90% wood pulp fibers and from about 5 to about 10% thermoplastic bicomponent binder fibers.

26. An absorbent structure capable of acquiring, distributing and storing aqueous body fluids which comprises:

(A). a fluid acquisition layer comprising a mixture of hydrophilic cellulosic fibers and thermoplastic material bonding said fibers together into a thermally bonded matrix providing vertical wicking of from about 1 to about 6 cm of artificial menstrual fluid; and (B) a primary fluid distribution layer comprising a mixture of hydrophilic cellulosic fibers and thermoplastic material bonding said fibers together into a thermally bonded matrix providing vertical wicking of from about 11 to about 16 cm of artificial menstrual fluid;

(C) a secondary fluid distribution layer in fluid communication with, and which can acquire aqueous body fluids from, said primary distribution layer, said secondary distribution layer comprising a mixture of hydrophilic cellulosic fibers and thermoplastic material bonding said fibers together into a thermally bonded matrix providing vertical wicking of from about 1 to about 6 cm of artificial menstrual fluid;

(D) a fluid storage layer in fluid communication with one of said primary and secondary distribution layers, and comprising from about 15 to 100% by weight of said storage layer of absorbent gelling material and from 0 to about 85% by weight of said storage layer of a carrier for said absorbent gelling material.

27. The absorbent structure of claim 26 in which at least two of layers (A), (B), (C) and (D) are integrated together by thermal bonding.

28. A catamenial product which comprises a fluid pervious topsheet made from an apertured formed film or nonwoven material; a fluid impervious back sheet and the absorbent structure of claim 26 positioned between said primary topsheet and said backsheet.

29. The product of claim 28 selected from the group consisting of pantiliners and incontinence pads.

30. The absorbent structure of claim 26 wherein said thermally bonded matrices of said layers (A) and (C) provide vertical wicking of from about 2 to about 4 cm of artificial menstrual fluid.

31. The absorbent structure of claim 30 wherein said layers (A) and (C) have a wet density in the range of from about 0.03 to about 0.07 g/co.

32. The absorbent structure of claim 30 wherein said layer (B) has a wet density in the range of from about 0.075 to about 0.15 g/cc.

33. The absorbent structure of claim 32 wherein said layer (B) has a wet density in the range of from about 0.10 to about 0.15 g/cc and wherein said storage layer (D) comprises absorbent gelling material in an amount of from about 80 to about 150 gsm.

34. The absorbent structure of claim 26 which further comprises a fibrous layer (E) adjacent said storage layer and comprising a mixture of hydrophilic cellulosic fibers and thermoplastic material bonding said fibers together into a thermally bonded matrix.

35. The absorbent structure of claim 34 wherein said thermally bonded matrices of each of said layers (A), (B), (C) and (E) are formed from a mixture of comprising from about 10 to 95% wood pulp fibers and from about 5 to about 90% thermoplastic binder fibers.

36. The absorbent structure of claim 29 wherein storage layer (D) comprises from about 30 to 100% absorbent gelling materials and from 0 to about 70% carrier.

37. The absorbent structure of claim 35 wherein said thermally bonded matrices of each of said layers (A), (B), (C) and (E) are formed from a mixture comprising from about 55 to about 90% wood pulp fibers and from about 10 to about 45% thermoplastic binder fibers.

38. The absorbent structure of claim 37 wherein said thermally bonded matrix of said layer (B) is formed from a mixture having a basis weight of from about 80 to about 180 gsm and comprising from about 85 to about 95% wood pulp fibers and from about 5 to about 15% thermoplastic binder fibers.

39. The absorbent structure of claim 37 wherein said thermally bonded matrix of said layer (B) is formed from a mixture having a basis weight of from about 50 to about 200 gsm and comprising from about 80 to about 90% wood pulp fibers and from about 10 to about 20% thermoplastic binder fibers.

40. The absorbent structure of claim 39 wherein storage layer (D) comprises from about 60 to 100% absorbent gelling materials and from 0 to about 40%, carrier.

41. The absorbent structure of claim 37 wherein said thermally bonded matrices of each of said layers (A) and (C) are formed from a mixture having a basis weight of from about 40 to about 60 gsm. and comprising from about 45 to about 90% wood pulp fibers; up to about 30% hydrophilic nonbonding thermoplastic fibers, and from about 5 to about 50% thermoplastic bicomponent binder fibers.

42. The absorbent structure of claim 41 wherein said thermally bonded matrices of each of said layers (A) and (C) are formed from a mixture having a basis weight of from about 45 to about 55 gsm and comprising from about 65 to about 90% wood pulp fibers, from about 10 to about 20% hydrophilic nonbonding thermoplastic fibers, and from about 10 to about 20% thermoplastic bicomponent binder fibers.

43. The absorbent structure of claim 41 wherein said thermally bonded matrix of said layer (E) is formed from a mixture comprising from about 85 to about 90% wood pulp fibers and from about 5 to about 10% thermoplastic bicomponent binder fibers.

44. A catamenial pad capable of acquiring, distributing and storing aqueous body fluids, which comprises:

(A) a fluid pervious topsheet selected from the group consisting of apertured formed film topsheets and high loft nonwoven topsheets;

(B) a fluid acquisition layer adjacent said topsheet, said acquisition layer comprising a mixture of hydrophilic cellulosic fibers and thermoplastic material bonding said fibers together into a thermally bonded matrix providing vertical wicking of from about 1 to about 6 cm of artificial menstrual fluid;

(C) an absorbent core in fluid communication with said fluid acquisition layer and having:

(1) a primary fluid distribution layer comprising a mixture of hydrophilic cellulosic fibers and thermoplastic material bonding said fibers together into a thermally bonded matrix providing vertical wicking of from about 8 to about 20 cm of artificial menstrual fluid;

(2) a secondary fluid distribution layer in fluid communication with, and which can acquire aqueous body fluids from, said primary distribution layer, said secondary distribution layer comprising a mixture of hydrophilic cellulosic fibers and thermoplastic material bonding said fibers together into a thermally bonded matrix providing vertical wicking of from about 1 to about 6 cm of artificial menstrual fluid;

(3) a fluid storage layer in fluid communication with said secondary distribution layer, and comprising from about 15 to 100% by weight of said storage layer of absorbent gelling material and from 0 to about 85% by weight of said storage layer of a carrier for said absorbent gelling material;

(4) a fibrous layer adjacent said storage layer and comprising a mixture of hydrophilic cellulosic fibers and thermoplastic material bonding said fibers together into a thermally bonded matrix;

(D) a fluid impervious backsheet.

45. The pad of claim 44 wherein said topsheet is an apertured formed film topsheet.

46. The pad of claim 44 having:

(1) a compressive force value in the dry state of about 300 g or less;

(2) an absolute recovery from compression value in the wet state of at least about 48 mm; and (3) a relative recovery from compression value in the wet state of at least about 65% of the initial pad width.

47. The pad of claim 46 having:

(1) a compressive force value in the dry state in the range of from about 100 to about 200 g;

(2) an absolute recovery from compression value in the wet state of from about 55 to about 65 mm; and (3) a relative recovery from compression value in the wet state of from about 75 to about 85% of the initial pad width.

48. The pad of claim 44 wherein said thermally bonded matrices of each of said layers (B) and (C)(2) provide vertical wicking of from about 2 to about 4 cm of artificial menstrual fluid.

49. The pad of claim 48 wherein said layers (B) and (C)(2) have a wet density in the range of from about 0.03 to about 0.07 g/cc.

50. The pad of claim 49 wherein said layer (C)(1) has a wet density in the range of from about 0.10 to about 0.15 g/cc and wherein said storage layer (C)(3) comprises absorbent gelling material in an amount of from about 80 to about 150 gsm.

51. The pad of claim 48 wherein said thermally bonded matrix of said layer (A) provides vertical wicking of from about 11 to about 16 cm of artificial menstrual fluid.

52. The pad of claim 51 wherein said thermally bonded matrices of each of said layers (B), (C)(1) (C)(2) and (C)(4) are formed from a mixture comprising from about 10 to 95% wood pulp fibers and from about 5 to about 90% thermoplastic binder fibers.

53. The pad of claim 52 wherein said thermally bonded matrix of said layer (C)(4) is formed from a mixture comprising from about 85 to about 90% wood pulp fibers and from about 5 to about 10% thermoplastic bicomponent binder fibers.

54. The pad of claim 52 wherein said thermally bonded matrix of said layer (C)(1) is formed from a mixture having a basis weight of from about 50 to about 200 gsm and comprising from about 80 to about 90% wood pulp fibers and from about 10 to about 20% thermoplastic bicomponent binder fibers.

55. The pad of claim 52 wherein said thermally bonded matrix of said layer (C)(1) is formed from a mixture having a basis weight of from about 80 to about 180 gsm and comprising from about 85 to about 95% wood pulp fibers and from about 5 to about 15% thermoplastic binder fibers.

56. The pad of claim 52 wherein said thermally bonded matrices of each of said layers (B), (C)(1) (C)(2) and (C)(4) are formed from a mixture comprising from about 55 to about 90% wood pulp fibers and from about 10 to about 45% thermoplastic binder fibers.

57. The pad of claim 56 wherein said thermally bonded matrices of each of said layers (B) and (C)(2) are formed from a mixture having a basis weight of from about 40 to about 60 gsm. and comprising from about 45 to about 90% wood pulp fibers; up to about 30% hydrophilic nonbonding thermoplastic fibers, and from about 5 to about 50% thermoplastic bicomponent binder fibers.

58. A catamenial pad capable of acquiring, distributing and storing aqueous body fluids, which comprises:

(A) a fluid pervious topsheet selected from the group consisting of apertured formed film topsheets and high loft nonwoven topsheets;

(B). a fluid acquisition layer adjacent said topsheet, said acquisition layer comprising a mixture of hydrophilic cellulosic fibers and thermoplastic material bonding said fibers together into a thermally bonded matrix;

(C) an absorbent core in fluid communication with said fluid acquisition layer and having:

(1) a primary fluid distribution layer comprising a mixture of hydrophilic cellulosic fibers and thermoplastic material bonding said fibers together into a thermally bonded matrix;

(2) a secondary fluid distribution layer in fluid communication with, and which can acquire aqueous body fluids from, said primary distribution layer, said secondary distribution layer comprising a mixture of hydrophilic cellulosic fibers and thermoplastic material bonding said fibers together into a thermally bonded matrix;

(3) a fluid storage layer in fluid communication with said secondary distribution layer, and comprising from about 15 to 100% by weight of said storage layer of absorbent gelling material and from 0 to about 85% by weight of said storage layer of a carrier for said absorbent gelling material;

(D) a fluid impervious backsheet;

(E) wherein the pad has:

(1) a compressive force value in the dry state of about 300 g or less;

(2) an absolute recovery from compression value in the wet state of at least about 48 mm; and (3) a relative recovery from compression value in the wet state of at least about 65% of the initial pad width.

59. The pad of claim 58 having:

(1) a compressive force value in the dry state in the range of from about 50 to about 300 g;

(2) an absolute recovery from compression value in the wet state of from about 48 to about 70 mm; and (3) a relative recovery from compression value in the wet state of from about 65 to about 90% of the initial pad width.

60. The pad of claim 58 having:

(1) a compressive force value in the dry state of about 200 g or less;

(2) an absolute recovery from compression value in the wet state of at least about 55 mm; and (3) a relative recovery from compression value in the wet state of at least about 75% of the initial pad width.

61. The pad of claim 60 having:

(1) a compressive force value in the dry state in the range of from about 100 to about 200 g;

(2) an absolute recovery from compression value in the wet state of from about 55 to about 65 mm; and (3) a relative recovery from compression value in the wet state of from about 75 to about 85% of the initial pad width.

62. The absorbent structure of claim 61 which further comprises a fibrous layer (C)(4) adjacent said storage layer (C)(3) and comprising a mixture of hydrophilic cellulosic fibers and thermoplastic material bonding said fibers together into a thermally bonded matrix.

63. The pad of claim 62 wherein said thermally bonded matrices of each of said layers (B), (C)(1) (C)(2) and (C)(4) are formed from a mixture comprising from about 55 to about 90% wood pulp fibers and from about 10 to about 45% thermoplastic binder fibers.

64. The pad of claim 63 wherein said thermally bonded matrices of each of said layers (B), (C)(2) and (C)(4) are formed from a mixture having a basis weight of from about 40 to about 60 gsm. and comprising from about 45 to about 90% wood pulp fibers; up to about 30% hydrophilic non-bonding thermoplastic fibers, and from about 5 to about 50% thermoplastic bicomponent binder fibers.

65. The pad of claim 63 wherein said thermally bonded matrix of said layer (C)(4) is formed from a mixture comprising from about 85 to about 90% wood pulp fibers and from about 5 to about 10% thermoplastic bicomponent binder fibers.

66. The pad of claim 63 wherein said thermally bonded matrix of said layer (C)(1) is formed from a mixture having a basis weight of from about 150 to about 200 gsm and comprising from about 80 to about 90% wood pulp fibers and from about 10 to about 20% thermoplastic bicomponent binder fibers.

67. The pad of claim 63 wherein said thermally bonded matrix of said layer (C)(1) is formed from a mixture having a basis weight of from about 160 to about 180 gsm and comprising from about 85 to about 95% wood pulp fibers and from about 5 to about 15% thermoplastic binder fibers.

* * * * *

UNITED STATES PATENT AND TRADEMARK OFFICE
CERTIFICATE OF CORRECTION

PATENT NO. : 5,607,414
DATED : March 4, 1997
INVENTOR(S) : Richards et al.

It is certified that error appears in the above-indentified patent and that said Letters Patent is hereby corrected as shown below:

In Col. 1, line 44, "or" should read --of--.

In Col. 22, line 60, "panty liners" should read --pantiliners--.

In Col. 34, line 18, "Claim 29" should read --Claim 35--.

Signed and Sealed this

Eighth Day of July, 1997

Attest:

BRUCE LEHMAN

*Attesting Officer*     *Commissioner of Patents and Trademarks*